(12) United States Patent
Yamazaki et al.

(10) Patent No.: US 7,148,200 B2
(45) Date of Patent: *Dec. 12, 2006

(54) METHOD FOR TREATING CANCER

(75) Inventors: Takayuki Yamazaki, Noda (JP); Fumio Sugawara, Niiza (JP); Keisuke Ohta, Noda (JP); Kazuyoshi Masaki, Sakado (JP); Kotaro Nakayama, Yotsukaido (JP); Kengo Sakaguchi, Tsukuba (JP); Noriyuki Sato, Sapporo (JP); Hiroeki Sahara, Sapporo (JP); Tatsuya Fujita, Sapporo (JP)

(73) Assignee: Toyo Suisan Kaisha, Ltd., Tokyo (JP)

( * ) Notice: Subject to any disclaimer, the term of this patent is extended or adjusted under 35 U.S.C. 154(b) by 311 days.

This patent is subject to a terminal disclaimer.

(21) Appl. No.: 10/678,193

(22) Filed: Oct. 2, 2003

(65) Prior Publication Data

US 2004/0067893 A1 Apr. 8, 2004

Related U.S. Application Data

(60) Division of application No. 09/934,874, filed on Aug. 22, 2001, now Pat. No. 6,770,629, which is a continuation-in-part of application No. PCT/JP00/00973, filed on Feb. 21, 2000.

(30) Foreign Application Priority Data

Feb. 26, 1999 (JP) ................................ 11-051397

(51) Int. Cl.
*A61K 31/70* (2006.01)
*C07G 3/00* (2006.01)
*C08B 37/00* (2006.01)
*C07H 11/00* (2006.01)
*C12N 9/99* (2006.01)

(52) U.S. Cl. ........................ 514/25; 536/4.1; 536/55; 536/118; 435/184

(58) Field of Classification Search ................ 514/25; 536/4.1, 55, 118; 435/184
See application file for complete search history.

(56) References Cited

U.S. PATENT DOCUMENTS

| | | | |
|---|---|---|---|
| 5,489,578 A * | 2/1996 | Rosen et al. ................ 514/61 |
| 5,695,752 A * | 12/1997 | Rosen et al. ............. 424/94.61 |
| 5,783,693 A * | 7/1998 | Bertozzi et al. ............ 536/124 |
| 6,395,886 B1 * | 5/2002 | Yamazaki et al. ............ 536/4.1 |
| 6,444,795 B1 * | 9/2002 | Yamazaki et al. ............ 536/4.1 |
| 6,518,248 B1 * | 2/2003 | Yamazaki et al. ............ 514/25 |
| 6,518,410 B1 * | 2/2003 | Yamazaki et al. ............ 536/4.1 |
| 6,770,629 B1 * | 8/2004 | Yamazaki et al. ............ 514/25 |
| 2002/0022597 A1 | 2/2002 | Yamazaki et al. |
| 2002/0028776 A1 * | 3/2002 | Yamazaki et al. ............ 514/23 |
| 2002/0028777 A1 | 3/2002 | Yamazaki et al. |
| 2002/0052327 A1 * | 5/2002 | Yamazaki et al. ............ 514/25 |
| 2002/0173471 A1 * | 11/2002 | Yamazaki et al. ............ 514/24 |

FOREIGN PATENT DOCUMENTS

| | | | |
|---|---|---|---|
| JP | 55-130996 A | * | 10/1980 |
| JP | 03-052815 A | * | 3/1991 |
| JP | 3-52816 | | 3/1991 |
| JP | 03-052816 A | * | 3/1991 |
| JP | 3-66603 | | 3/1991 |
| JP | 03-066603 A | * | 3/1991 |
| JP | 60-040159 A | * | 9/1991 |
| JP | 03-246203 A | * | 11/1991 |
| JP | 7-242691 | | 9/1995 |
| JP | 9-268198 A | | 10/1997 |
| JP | 11-106395 | | 4/1999 |
| JP | 11-106395 A | * | 4/1999 |
| JP | 2000-143516 | | 5/2000 |
| WO | WO 91/02521 | | 3/1991 |
| WO | WO 97/40838 A1 | | 11/1997 |
| WO | WO 00/53190 | | 9/2000 |

OTHER PUBLICATIONS

Peer et al., "Synthesis of an L-Fucose-Derived Cyclic Nitrone and its Conversion to α-L-Fucosidase Inhibitors," *Helvetica Chemica Acta*, 82(7), 1044-1065 (Jul. 7, 1999).*

(Continued)

*Primary Examiner*—L. E. Crane
(74) *Attorney, Agent, or Firm*—Frishauf, Holtz, Goodman & Chick, P.C.

(57) ABSTRACT

A method for treating a cancer. The cancer excluding an adenocarcinoma and being epithelioma, glioma, sarcoma, melanoma, lymphoma or leukemia; or the cancer is an adenocarcinoma cancer excluding colon cancer, lung cancer and gastric cancer. The method comprises administering to a subject in need thereof and suffering from cancer, a pharmaceutically effective amount of at least one sulfoquinovosylacylglycerol compound represented by formula (1):

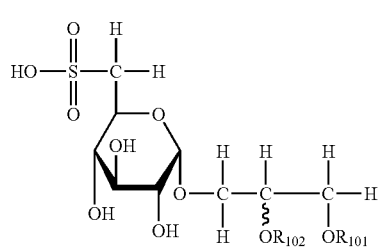

(1)

wherein $R_{101}$ represents an acyl residue of an unsaturated fatty acid and $R_{102}$ represents a hydrogen atom and/or at least one pharmaceutically acceptable salt thereof.

12 Claims, 7 Drawing Sheets

OTHER PUBLICATIONS

Sanders et al., "Synthesis of Sulfated Trisaccharide Ligands for the Selectins," *Tetrahedron*, 53(48), 16391-16422 (Dec. 1, 1997).*

Arasappan et al., "Regiospecific 4, 6-Functionalization of Pyranosides via Dimethylboron Bromide-Mediated Cleavage of Phthalide Orthoesters," *J.American Chemical Society*, 117(1), 177-183 (Jan. 11, 1995).*

Thiem et al., "Synthesen von Methyl-4-O-(β-D-curaocsyl)-α-D-curamicosid, dem Glycosid der Disaccharideinheit E-F von Flambamycin und Isomeren," *Justus Liebig's Annalen der Chemie*, 1987(4), 289-295 (Apr. 1987).*

Fujimaki et al., "Conversion of 1, 6-Anhydromaltose into Pseudodisaccharides Containing Aminocyclitols as Constituent," *Agricultural & Biological Chemistry*, 44(9), 2055-2059 (Sep. 1980).*

Tulloch et al., "Combination and Positional Distribution of Fatty Acids in Plant Sulfolipids," *Hoppe-Seyler's Zeitschrift Physiol. Chem.*, 354, 879-889 (Aug. 1973).*

Fusetani et al., "Structures of Two Water Soluble Hemolysins Isolated from the Green Alga *Ulva pertusa,*" *Agricultural and Biological Chemistry*, 39(10), 2021-2025 (Oct. 1975).*

Kitagawa et al., "Sulfoglycolipid from Sea Urchin *Anthocidaris vrassisspina* A. Agassiz," *Chemical & Pharmaceutical Bulletin*, 27(8), 1934-1937 (Aug. 1979).*

Gustafson et al., "AIDS-Antiviral Sulfolipids From Cyanobacteria (Blue-Green Algae)," *J. National Cancer Institute(USA)*, 81(16), 1255-1258 (Aug. 16, 1989).*

Adebodun et al., "Spectroscopic Studies of Lipids and Biological Membranes: Carbon-13 and Proton Magic-Angle Sample-Spinning Nuclear Magnetic Resonance Study of Glycolipid-Water Systems," *Biochemistry*, 31(18), 4502-4509 (May 1992).*

Gage et al., "Comparison of Sulfoquinovosyl Diacylglycerol from Spinach and the Purple Bacterium *Rhodobacter sphaeroides* by Fast Atom Bombardment Tandem Mass Spectrometry," *Lipids*, 27(8), 632-636 (Aug. 1992).*

Morimoto et al., "Studies on Glycolipids. VII. Isolation of Two New Sulfoquinovosyl Diacylgycerols from the Green Alga *Chlorella vulgaris,*" *Chemical & Pharmaceutical Bulletin*, 41(9), 1545-1548 (Sep. 1993).*

Amarquaye et al., "A New Glycolipid from *Byrsonima crassifolia,*" *Planta Medica*, 60(1), 85-86 (Feb. 1994).*

Murakami et al., "Enzymatic Transformation of Glyceroglycolipids into sn- 1 and sn- 2 Lysoglyceroglycolipids by Use of *Rhizopus arrhizus* Lipase," *Tetrahedron*, 50(7), 1993-2002 (Feb. 14, 1994).*

Vishwanath et al., "Interaction of Plant Lipids with 14 kDa Phospholipase $A_2$ Enzymes," *Biochemical Journal*, 320(1), 93-99 (Nov. 15, 1996).*

Golik et al., "Isolation and Structure Determination of Sulfonoquinovosyl Dipalmitoyl Glyceride, a P-Selectin Receptor Inhibitor from the Alga *Dictyochloris Frangrans, Journal of Natural Products*, 60(4), 387-389 (Apr. 1997).*

Väsänge et al., "A Sulfonoglycolipids from the Fern *Polypodium decumanum* and its Effect on the Platelet Activating-factor Receptor in Human Neutrophils," *Journal of Pharmaceutical Pharmacology*, 49(5), 562-566 (May 1997).*

Kim et al., "Structural Identification of Glycerolipid Molecular Species Isolated from Cyanobacterium *Synechocytis* sp. PCC 6803 Using Fast Atom Bombardment Tandem Mass Spectrometry," *Analytical Biochemistry*, 267, 260-270 (1999).*

Mizushina et al., "Search and Structural Identification of Inhibitory Substance on DNA Polymerase of Higher Organisms," published in *A Collection of Summaries of Lectures at Convention of Natural Organic Compounds*, published by Prof. K. Sakai (Kyushu University) and the Organizing Committee of the 40th Symposium on the Chemistry of Natural Products, Fukuoka, Japan, Aug. 31, 1998, only pp. 493-498 supplied.*

H Nakane & K Ono, "Inhibitor of DNA Polymerase Activity," *Metabolism*, 28(12), 1027-1034 (1991).*

Pugh et al. (eds.), *Stedman's Medical Dictionmary, 27the Ed.*), Lippincott, Williams and Wilkins, Philadelphia, PA, 2000, only p. 24 supplied.*

Mizushina, Yoshiyuki, et al., "Studies on Inhibitors of Mammalian DNA Polymerase alpha and beta," Biochemistry Pharmacology, 55, 537-541 (1998).*

Akio Ogana et al., Sulfated Glycoglycerolipid from Archaebacterium Inhibits Eukaryotic DNA Polymerase α, β and Retroviral Reverse Transcriptase and Affects Methyl Methanesulfonate Cytotoxicity, *International Journal of Cancer*, 76, 512-518 (1998).

Gerhard Kretzschmar et al., "Short Synthesis of Sulfatide- and SQDG-Mimetics as Small Molecular Weight Selectin inhibitors", *Tetrahedron*, 54, 15189-15198 (1998).

Bernd Meyer et al., Syntheses of Benzyl 6-O-Sulfo-β-D-glucopyranoside Salts and Their 6S-Deuterated Analogues. Conformational Preferences of Their (Sulfonyloxy)methyl Group, *Journal of Organic Chemistry*, 55, 902-906 (1990).

Byeng Wha Son; "Glycolipids from *Gracularia verrucosa*", Phytochemistry, vol. 29, No. 1, 1990; pp. 307-309.

Shirahashi Hideaki et al.; "Isolation and Identification of Antitumor-Promoting Principles from the Fresh-Water Cyanobacterium *Phormidium tenus*", Chem. Pharm. Bull., vol. 41, No. 9, (1993) pp. 1664-1666, (Sep. 1993).

Morimoto, Takashi et al.; "Studies on Glycolipids. VII. Isolation of Two New Sulfoquinovosyl Diacylglycerols from the Green Alga *Chlorella vulgaris*", Chem. Pharm. Bull. vol. 41,No. 9, 1993; pp. 1545-1548, (Sep. 1993).

Michael Keusgen et al.; "Sulfoquinovosyl Diacylglycerols from the Alga *Heterosigma carterase*", Lipids, vol. 32,No. 10; 1997; pp. 1101-1102.

Luca Rastrelli et al., "Glycolipids from *Byrsonima crassifolia*"; Phytochemistry, vol. 45, No. 4, 1997; pp. 647-650.

Sahara,H. et al.; "In vivo anti-tumour effect of 3'-sulfoquinovosyl-1'-monoacylglyceride isolated from sea urchin (*Stronglyocentrotus intermedius*) interstine"; British Journal of Cancer, vol. 75,No. 3, 1997; pp. 324-332.

Ohta, Keisuke et al.; "Sulfoquinovosyldiacylglycerol, KM043, a New Potent Inhibitor of Eukaryotic DNA Polymeraes and HIV-Reverse Transcriptase Type 1 from Marine Red Alga, *Gigartina tenells*"; Chem. Pharm. Bull., vol. 46,No. 4; 1998; pp. 684-686, (Apr. 1998).

S. Kashima et al., "A Study of Polymerase Inhibitors of Higher Plants", Nippon Nogeikagaku Kaisha, vol. 72, Mar. 5, 1998, p. 82.

Yoshiyuki Mizushina, Shonen Yoshida, Akio Matsukage and Kengo Sakaguchi, "The Inhibiting Action of Fatty Acids on DNA Polymerase β", *Biochimica et Biophysica Acta.*, 1336, (1997), 509-521.

Dana M. Gordon et al., "Synthesis of a Cyanobacterial Sulfolipid: Confirmation of Its Structure, Stereochemistry, and Anti-HIV-1 Activity", *J. Amer. Chem. Soc.*, 114, 659-663 (1992).

Roy Gigg et al., "Synthesis of 3-O-(6-Deoxy-6-sulpho-α-D-glucopyranosyl)-1,2-di-O-hexadecanoyl-L-glycerol, 'Sulphoquinovosyl Diglyceride'", *Journal of the Chemical Society Perkin Transaction I*, 2490-2493 (1980).

Pham Quang Liem et al., "Structures, teneurs et compositions des esters sulfuriques, sulfoniques, phosphoriques des glycosyldiglycerides de trois fucasees", *Biochimie*, 58, 1367-1380 (1976), includes an English-language summary.

* cited by examiner

METHOD FOR TREATING CANCER

CROSS-REFERENCE TO RELATED APPLICATIONS

This is a Divisional Application of application Ser. No. 09/934,874, filed Aug. 22, 2001, now U.S. Pat. No. 6,770,629, which is a continuation-in-part of PCT Application No. PCT/JP00/00973, filed Feb. 21, 2000, which was not published under PCT Article 21(2) in English. The entire contents of U.S. application Ser. No. 09/934,874 and International application PCT/JP00/00973 are hereby incorporated by reference herein.

This application is based upon and claims the benefit of priority from the prior Japanese Patent Application No. 11-051397, filed Feb. 26, 1999, the entire contents of which are incorporated herein by reference.

BACKGROUND OF THE INVENTION

1. Field of the Invention

The present invention relates to a medicament containing at least one compound selected from the group consisting of sulfopyranosylacylglycerol derivatives and pharmaceutically acceptable salts thereof, as an active ingredient.

2. Description of the Related Art

Sulfur-containing glycolipids contained in natural products derived from, e.g., algae and higher plants are known to have physiological activities.

For example, in a document of Ohta et al. (Chemical & Pharmaceutical Bulletin, 46(4), (1998)), it is described that a specific sulfoquinovosyldiacylglycerol derivative derived from red algae, *Gigartina tenella*, exhibits not only inhibitory activities against DNA polymerases α and β of higher organisms but also an HIV-derived reverse-transcriptase inhibitory activity. The sulfoquinovosyldiacylglycerol derivative disclosed in the Ohta document is the one whose fatty acid that bonded, through ester-bond, at the C1 carbon atom of the glycerol is an unsaturated fatty acid having 20 carbon atoms with 5 double bonds, and whose another fatty acid that bonded at the C2 carbon atom of the glycerol is a saturated fatty acid having 16 carbon atoms.

Furthermore, in a document of Mizushina et al. (Biochemical Pharmacology 55, 537–541 (1998)), it is described that a mixture of specific sulfoquinovosyldiacylglycerol derivatives derived from a pteridophyte exhibits inhibitory activities against a calf DNA polymerase α and a rat DNA polymerase β, however, the mixture has no effect upon an HIV-derived reverse-transcriptase activity.

On the other hand, in a document of Sahara et al. (British Journal of Cancer, 75(3), 324–332 (1997)), it is described that a fraction of sulfoquinovosylmonoacylglycerols contained in an acetone extract from a sea urchin intestine exhibits anticancer activities in-vivo and in-vitro. However, the sulfoquinovosylmonoacylglycerol fraction for which Sahara found the anticancer activities principally contains sulfoquinovosylmonoacylglycerol having, bonded thereto through an ester-bond, a saturated fatty acid with 16 carbon atoms. In the sulfoquinovosylmonoacylglycerol fraction, sulfoquinovosylmonoacylglycerols whose acyl moiety is that of an unsaturated fatty acid, are contained only in an extremely small amount. In addition, Sahara et al. have not yet investigated on anticancer activities with respect to individual components contained in the sulfoquinovosylmonoacylglycerol mixture.

Furthermore, National Patent Publication No. 5-501105 describes that a sulfoquinovosyldiacylglycerol derivative has an anti-virus activity. More specifically, it discloses that the derivative has an anti-HIV (human immunodeficiency virus) activity, however it does not disclose that the derivative has DNA polymerase inhibitory activities and anticancer activities.

BRIEF SUMMARY OF THE INVENTION

An object of the present invention is to provide a medicament containing a sulfopyranosylacylglycerol derivative as an active ingredient.

The present inventors found that specific sulfopyranosylacylglycerol derivatives have medicinal activities and achieved the present invention. The present invention provides a medicament containing, as an active ingredient, at least one compound selected from the group consisting of:

compounds represented by the following General Formula (1):

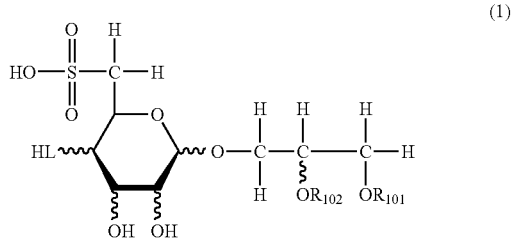

(1)

wherein $R_{101}$ represents an acyl residue of an unsaturated higher fatty acid, and $R_{102}$ represents a hydrogen atom or an acyl residue of an unsaturated higher fatty acid; and pharmaceutically acceptable salts thereof.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
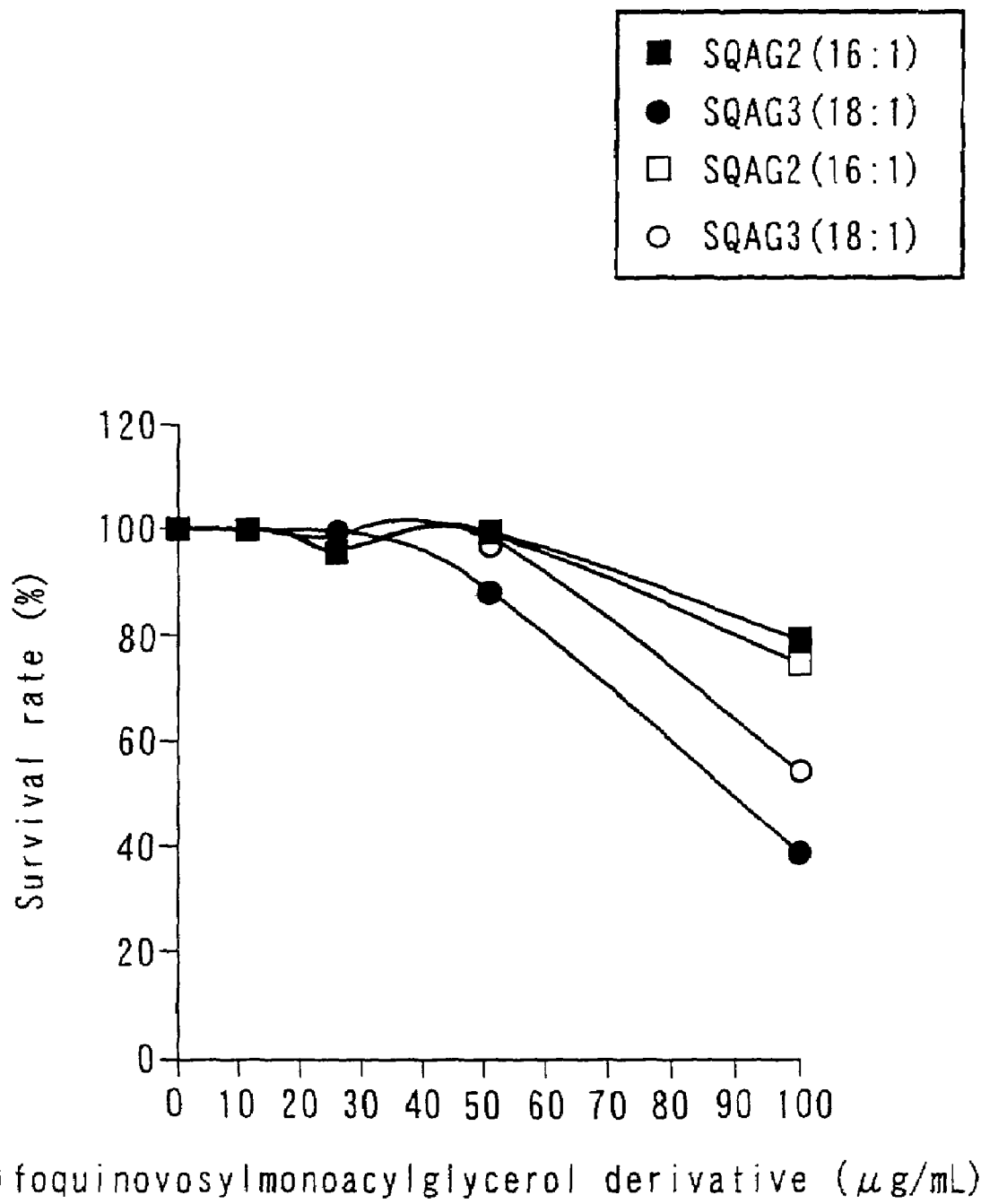
FIG. 1 shows anticancer activities of medicaments of the present invention against tumor cells.

In the specification, the term "carbon atoms" of a protecting group refers to the number of carbon atoms assuming that the protecting group is unsubstituted. To be more specific, when the group represented by $R^6$ is a substituted alkyl group, its number of carbon atoms is that of the alkyl group itself, and the number of carbon atoms of the substituent on the alkyl group is not counted. The same conditions are applicable to the case where the protecting group is other than the alkyl group.

First, the sulfopyranosylacylglycerol derivative represented by General Formula (1) and contained in the medicament of the present invention as an active ingredient will be more specifically explained.

In the sulfopyranosylacylglycerol derivative represented by General Formula (1), the pyranose, which is a sugar skeleton constituting the pyranoside, may include α-D-quinovose (i.e., 6-deoxy-α-D-glucose), β-D-quinovose (i.e., 6-deoxy-β-D-glucose), α-D-fucose (i.e., 6-deoxy-α-D-galactose), β-D-fucose (i.e., 6-deoxy-β-D-galactose), α-D-rhamnose (i.e., 6-deoxy-α-D-mannose) and β-D-rhamnose (i.e., 6-deoxy-β-D-mannose).

The absolute configuration of the carbon (asymmetric carbon) at the 2-position of the glycerol moiety may be either the S- or R-configuration.

The sugar skeleton of the pyranoside may be either a boat or chair configuration. However, the chair configuration is preferable in view of stability.

In the sulfopyranosylacylglycerol derivative represented by General Formula (1), $R_{101}$ represents an acyl residue of an unsaturated higher fatty acid.

The fatty acid giving the acyl residue represented by $R_{101}$ may be a straight-chain or branched-chain, unsaturated higher fatty acid. From the viewpoint of using the compound represented by General Formula (1) as a medicament, the straight-chain unsaturated higher fatty acid is preferably used.

The acyl residue of the straight-chain unsaturated higher fatty acid has 14–26 carbon atoms (preferably even number of 14–26) with 1–6 unsaturated bonds. The acyl residue of the straight-chain unsaturated higher fatty acid is represented by Formula: R—C (=O)—, where R is a straight-chain aliphatic unsaturated hydrocarbon group of 13–25 carbon atoms (preferably, an odd number of 13–25), and 1–6 unsaturated bonds are included in the hydrocarbon group.

In the sulfopyranosylacylglycerol derivative represented by General Formula (1), $R_{102}$ represents a hydrogen atom or an acyl residue of an unsaturated higher fatty acid. In particular, $R_{102}$ preferably represents a hydrogen atom in consideration of an anti-cancer activity. When $R_{102}$ is an acyl residue of the unsaturated higher fatty acid, the same fatty acid giving an acyl residue as defined in $R_{101}$ may be selected. $R_{101}$ and $R_{102}$ may be the same or different acyl residue.

Now, a method of preparing the sulfopyranosylacylglycerol derivatives of the present invention will be explained below.

The sulfopyranosylacylglycerol derivatives of the present invention can be prepared via (Step A) to (Step J) in accordance with the reaction procedure shown in Scheme 1 below:

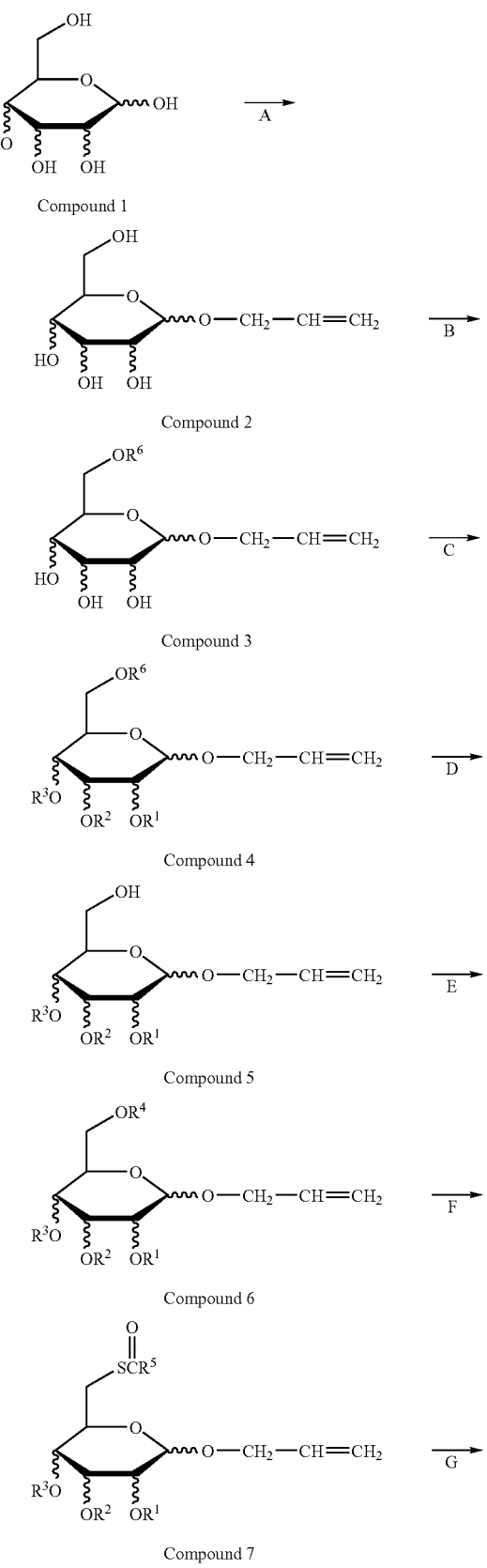

Scheme 1

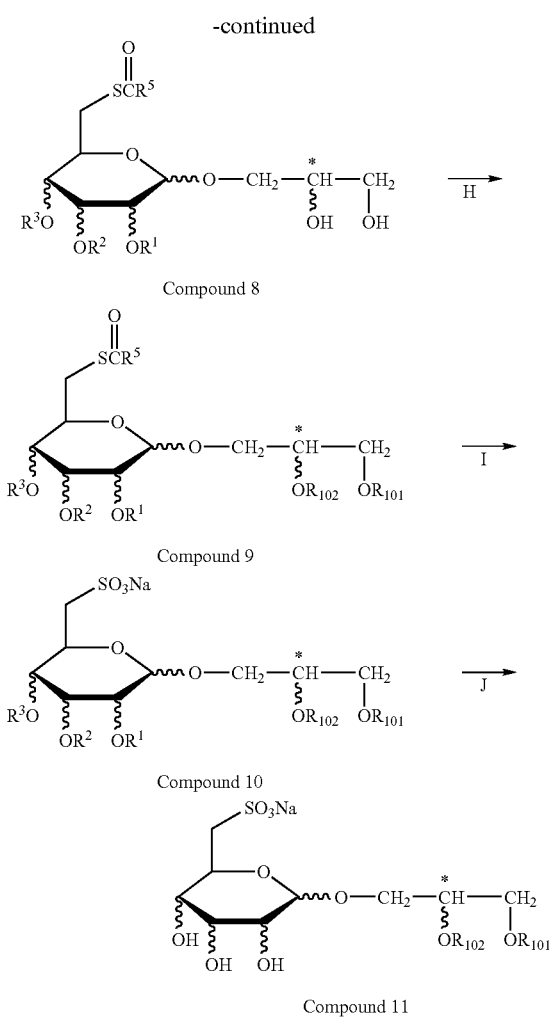

(Step A) The hydroxyl group bonded to the C1 carbon of the pyranose is converted into a 2-propenyl group. (Step B) The hydroxyl group of the C6 carbon of the pyranose is protected. (Step C) The hydroxyl groups bonded to the C2, C3 and C4 carbons of the pyranose are protected. (Step D) The protecting group of the C6 carbon previously protected is deprotected. (Step E) The hydroxyl group bonded to the C6 carbon is substituted with a group (for example, an alkylsulfonyloxy group or arylsulfonyloxy group) which can be converted to a carbonylthio group. (Step F) The C6 carbon is converted into a carbonylthio group. (Step G) The 2-propenyl group bonded to the C1 carbon is converted into a diol. (Step H) Both of the hydroxyl groups or only the hydroxyl group at the 1-position of the diol thus obtained are/is esterified with a desired unsaturated higher fatty acid. (Step I) The carbonylthio group at the C6 carbon is converted into a sulfonate salt. (Step J) The protecting groups of C2, C3 and C4 carbons of the sulfonate salt obtained are deprotected. As a result, a salt of a sulfopyranosylacylglycerol derivative of the present invention can be produced. The salt thus obtained is subjected to titration with an acid such as hydrochloric acid to give the sulfopyranosylacylglycerol derivative of the present invention.

The aforementioned Steps A–J will be further explained in detail.

In Step A, the 2-propenylation is carried out by reacting the pyranose with allyl alcohol in the presence of a strong acid, such as trifluoromethanesulfonic acid, usually at room temperature to 100° C., preferably from 80 to 90° C., for a half day to two days. However, the reaction time varies depending upon the reaction conditions.

In Step B, the hydroxyl group bonded to the C6 carbon is protected to obtain the compound to which —$OR^6$ is bonded at the C6 carbon (where $R^6$ represents an alkyl or substituted silyl group).

As the compound capable of protecting the hydroxyl group, a compound can be used which can provide an alkyl group or substituted silyl group as the $R^6$ group.

Examples of the alkyl group represented by $R^6$ preferably include bulky and substituted alkyl groups. The substituents of the bulky and substituted alkyl groups include methyl and phenyl groups. The specific examples of the substituted alkyl group include t-butyl and trityl groups.

When the group represented by $R^6$ represents a substituted silyl group, examples of substituents of the substituted silyl group include lower alkyl groups, preferably alkyl groups having 1–4 carbon atoms (for example, methyl, ethyl, isopropyl and t-butyl groups); and aryl groups, preferably aryl groups having 6 carbon atoms (for example, a phenyl group). The substituted silyl group represented by $R^6$ preferably includes tri-substituted silyl groups, more preferably, a t-butyldiphenylsilyl group.

When the compound 3, where $R^6$ represents an alkyl group, is to be obtained, the protection of the hydroxyl group in Step B can be carried out by adding a compound represented by $R^6$—X (where $R^6$ represents the alkyl group defined above, and X represents a halogen atom such as chlorine atom) to a solution of the compound 2 dissolved in an organic solvent, such as anhydrous pyridine, and reacting the solution mixture at room temperature in the presence of a catalyst such as p-dimethylaminopyridine (DMAP). As the compound $R^6$—X, trityl chloride is preferably used in view of manufacturability and reactivity.

When the compound 3, where $R^6$ represents a substituted silyl group, is to be obtained, t-butyldiphenylsilyl chloride, for example, is used as the compound $R^6$—X, and the reaction is carried out usually in the presence of a catalyst, such as imidazol, at room temperature for a half day to two days. Note that the reaction time varies depending upon the reaction conditions.

In Step C, the hydroxyl groups bonded to the C2, C3 and C4 carbons are protected and converted into —$OR^1$, —$OR^2$ and —$OR^3$, respectively, where $R^1$ to $R^3$ independently represent an alkyl or substituted silyl group. The protection of these hydroxyl groups can be carried out by activating, with sodium hydride, the hydroxyl groups bonded to the C2, C3 and C4 carbons of the compound 3 dissolved in an organic solvent, such as N,N-dimethylformamide (DMF), and reacting with the compound capable of protecting these hydroxyl groups at room temperature.

As the compound capable of protecting the hydroxyl groups, benzyl bromide, p-methoxybenzyl bromide, t-butyldimethylsilyl chloride or triethylsilyl chloride may be used.

The reaction using the compound capable of protecting the hydroxyl groups can be carried out under a suitable reaction condition for each of the protecting groups.

The deprotection of the protecting group bonded to the C6 carbon in Step D may be carried out by reacting a solution of the compound 4 dissolved in an organic solvent, such as methanol, in the presence of a catalyst, such as p-toluenesulfonic acid, generally for 12 hours to one day at room temperature. The reaction time varies depending upon the reaction conditions.

In Step E, $R^4$, that is, an alkylsulfonyl or arylsulfonyl group is bonded to the hydroxyl group at the C6 carbon of the compound 5, so that the hydroxyl group is converted into —$OR^4$ to give the compound 6.

The reaction to give the —$OR^4$ group is performed by adding a compound having the alkylsulfonyl group or a compound having the arylsulfonyl group to a solution of the compound 5 dissolved in an organic solvent, and reacting them. The alkyl group of the compound having the alkylsulfonyl group preferably includes unsubstituted alkyl groups, more preferably, lower alkyl groups, much more preferably, alkyl groups having 1–2 carbon atoms (methyl and ethyl groups). The compound having an alkylsulfonyl group can be represented by $R^{4'}$—X (where $R^{4'}$ represents an alkylsulfonyl group, and X represents a halogen atom). Specific examples include methanesulfonyl chloride and ethanesulfonyl chloride.

On the other hand, the aryl group of the compound having the arylsulfonyl group may include unsubstituted and substituted aryl groups, preferably aryl groups having 6 carbon atoms (e.g., a phenyl group). In the case of the substituted aryl group, examples of the substituent thereof include p-methyl and p-methoxy groups. Examples of the compound having an arylsulfonyl group include compounds represented by $R^{4''}$—X (where $R^{4''}$ represents an arylsulfonyl group, and X represents a halogen atom). Specific examples include p-toluenesulfonyl chloride, p-methoxybenzenesulfonyl chloride and benzenesulfonyl chloride.

Of the compounds having an alkylsulfonyl or arylsulfonyl group, a compound having a tosyl group is preferably used from the viewpoint of reaction facility.

In the reaction of Step E, as an organic solvent, pyridine or dichloromethane may be used.

The reaction mentioned above may be performed, as the case may be, in the presence of a catalyst, such as DMAP, at room temperature for 2 hours to one day. The reaction time varies depending upon the reaction conditions.

In Step F, the sulfonyloxy group (—$OR^4$) of the compound 6 is replaced with a carbonylthio group represented by —SC(=O)$R^5$, where $R^5$ represents a hydrogen atom, an alkyl or aryl group.

In the reaction, a compound capable of substituting the alkylsulfonyloxy or arylsulfonyloxy group of the compound 6 with the carbonylthio group, is allowed to react in an organic solvent to give a compound 7. Hereinafter, this compound will be referred to as "O-substituted→S-substituted compound".

Examples of the O-substituted→S-substituted compound include alkali metal salts and alkali earth metal salts of a thiocarboxylic acid. Examples of the thiocarboxylic acid include thioformic acid, lower thiocarboxylic acids, preferably aliphatic thiocarboxylic acids each having 1–5 carbon atoms in its aliphatic hydrocarbon moiety (for example, thioacetic acid or thiopropionic acid), and aromatic thiocarboxylic acids each having 6–10 carbon atoms in its aromatic hydrocarbon moiety (for example, thiobenzoic acid).

The alkali metal that forms a salt with the thiocarboxylic acid includes potassium and sodium. The alkali earth metal includes magnesium and calcium.

Of the above-mentioned O-substituted→S-substituted compounds, salts of thioacetic acid may be preferably used since a reaction can proceed stably and the sulfur atom can be easily oxidized in a later step.

Examples of an organic solvent used in the reaction include alcohols, preferably lower alcohols, (for example, methanol, ethanol and propanol), N,N-dimethylformamide and dimethylsulfoxide.

The aforementioned reaction may be performed usually at room temperature to the boiling point of a solvent to be used while stirring for one hour to one day. Note that the reaction time varies depending upon the reaction conditions.

The dihydroxylation of Step G may be performed by adding an oxidizing agent, such as osmium tetraoxide, to a solution of the compound 7 dissolved in a solvent mixture, such as a mixture of t-butanol and water, and then reacting the resultant mixture in the presence of a re-oxidizing agent, such as trimethylamine N-oxide, at room temperature for one hour to one day. Note that the reaction time varies depending upon the reaction conditions.

By the esterification of Step H, a sulfopyranosylacylglycerol derivative having a desired unsaturated higher fatty acid bonded, through an ester-bond, to its glycerol moiety can be obtained.

This reaction can be carried out by adding an unsaturated higher fatty acid corresponding to a final product to a solution of the compound 8 dissolved in a suitable organic solvent, such as dichloromethane, and then reacting the resultant mixture, if necessary, in the presence of a suitable catalyst, such as ethyldimethylaminopropylcarbodiimide (EDCI)-DMAP.

In the reaction of Step H, as the fatty acid to be added, use may be made of an unsaturated higher fatty acid whose acyl group is that represented by $R_{101}$ of General Formula (1).

In the reaction of Step H, the compound 9 is obtained in the form of a mixture of a diacylester and a monoacylester. The diacylester herein is represented by Formula (1) of the present invention where each of $R_{101}$ and $R_{102}$ is an acyl residue of the unsaturated higher fatty acid added. The monoacylester herein has the acyl residue of the unsaturated higher fatty acid added, as the $R_{101}$ only. Two or more unsaturated higher fatty acids may be added, if desired, in the reaction of Step H. In this case, the resultant mixture contains diacylesters represented by General Formula (1) where $R_{101}$ and $R_{102}$ are the same or different acyl residues, and monoesters having different acyl residues as $R_{101}$.

If necessary, the mixture of the monoesters and diesters can be isolated from each other by, for example, chromatography, and subjected to the next reaction Step I.

Furthermore, if desired, by reacting a monoester obtained in Step H with a fatty acid having a different acyl residue from the acyl residue ($R_{101}$) of the monoester, it is possible to obtain a diester where $R_{102}$ and $R_{101}$ are different acyl residues. This additional esterification step may be performed under the same conditions as those of Step H except that a different fatty acid is used.

In Step I, the conversion into a sulfonate salt can be carried out by adding an oxidizing agent, such as OXONE ($2KHSO_5+KHSO_4+K_2SO_4$) or molybdenum oxidizing agent (for example, hexaammonium heptamolybdate), into a solution of the compound 9 dissolved in an organic solvent, which is buffered with acetic acid and potassium acetate, and then allowing the resultant mixture to react at room temperature.

The deprotection of the protecting groups bonded to carbons at the C2 to C4 carbons in Step J can be carried out by a method suitable for a protecting group to be used and capable of maintaining a double bond of the unsaturated fatty acid. For example, when the protecting group is a silyl group, deprotection can be made by using acid catalyst (e.g., trifluoroacetic acid).

Note that the pyranosyl moiety of a starting material usually takes α- and β-anomer configurations in a solution. Therefore, the product in each step results in a mixture of α- and β-anomers. The mixture is separated into α- and β-anomers by chromatography. Furthermore, depending upon a type of the sugar, it is helpful to carry out a benzilydenation after Step A, thereby to separate an anomer by crystallization.

Now, we will explain the medicament of the present invention containing at least one compound selected from the group consisting of sulfopyranosylacylglycerol derivatives of the present invention and pharmaceutically acceptable salts thereof, as an active ingredient.

The sulfopyranosylacylglycerol derivative serving as an active ingredient for the medicament of the present invention may be an isomer having quinovose, rhamnose or fucose as the pyranose constituting the pyranosyl moiety. The derivative may be an isomer in which the pyranosyl moiety is bonded to glyceridyl moiety with an α- or β-configuration. The derivative may be an isomer regarding the asymmetric carbon at the C2 carbon of the glyceridyl moiety. The medicament of the present invention may include one of these isomers alone or in combination of two or more isomers as long as they do not adversely affect the activity.

In the present invention, the medicinal use includes a DNA polymerase inhibitor and an anticancer agent.

Examples of the pharmaceutically acceptable salts employed in the medicament of the present invention include, but not limited to, a salt of a monovalent cation such as a sodium or potassium ion. Hereinafter, the compounds of the group consisting of sulfopyranosylacylglycerol derivatives and pharmaceutically acceptable salts thereof are sometimes referred to as "medicinally active substance of the present invention".

The medicinally active substance of the present invention can be orally or parenterally administered. Medicinally active substance of the present invention can be combined with, for example, a pharmaceutically acceptable excipient or diluent depending on an administration route thereby to form a medicinal formulation.

The forms of the agent suitable for oral administration include, solid-, semi-solid, liquid- and gas-states. Specific examples include, but not limited to, tablet, capsule, powder, granule, solution, suspension, syrup and elixir agents.

In order to formulate the medicinally active substance of the present invention into tablets, capsules, powders, granules, solutions or suspensions, the substance is mixed with a binder, a disintegrating agent and/or a lubricant, and, if necessary, the resultant is mixed with a diluent, a buffer, a wetting agent, a preservative and/or a flavor, by a known method. Examples of the binder include crystalline cellulose, cellulose derivatives, cornstarch and gelatin. Examples of the disintegrating agent include cornstarch, potato starch and sodium carboxymethylcellulose. Examples of the lubricant include talc and magnesium stearate. Furthermore, additives such as lactose and mannitol may also be used as long as they are used conventionally.

Moreover, the medicinally active substance of the present invention may be administered in the form of aerosol or inhalant, which is prepared by charging the active substance of liquid- or fine powder-form, together with a gaseous or liquid spraying agent, and, if necessary, a known auxiliary agent such as a wetting agent, into a non-pressurized container such as an aerosol container or a nebulizer. As the spraying agent, a pressurized gas, for example, dichlorofluoromethane, propane or nitrogen may be used.

For parenteral administration, the medicinally active agent of the present invention can be injected by, for example, rectal administration or injection.

For rectal administration, a suppository may be used. The suppository may be prepared by mixing the medicinally active substance of the present invention with an excipient that can be melted at body temperature but is solid at room temperature, such as cacao butter, carbon wax or polyethylene glycol, and molding the resultant material, by a known method.

For the administration by injection, the medicinally active agent of the present invention can be injected hypodermically, intracutaneously, intravenously or intramuscularly. An injection preparation may be formulated by dissolving, suspending or emulsifying the medicinally active substance of the invention into an aqueous or non-aqueous solvent such as a vegetable oil, a synthetic glyceride with a fatty acid, an ester of a higher fatty acid or propylene glycol by a known method. If desired, a conventional additive such as a solubilizing agent, an osmoregulating agent, an emulsifier, a stabilizer or a preservative, may be added to the preparation.

For formulating the medicinally active substance of the invention into solutions, suspensions, syrups or elixirs, a pharmaceutically acceptable solvent such as sterilized water for injection or normalized physiological saline solution may be used.

The medicinally active substance of the invention may be used together with a pharmaceutically acceptable compound having another activity, to prepare a medicinal preparation.

The dose of the medicinally active substance of the present invention may be appropriately set or adjusted in accordance with an administration form, an administration route, a degree or stage of a target disease, and the like. For example, in the case of oral administration, a dose of the medicinally active substance may be set at 1–10 mg/kg body weight/day. In the case of administration by injection, a dose of the medicinally active substance may be set at 1–5 mg/kg body weight/day. In the case of rectal administration, a dose of the medicinally active substance may be set at 1–5 mg/kg body weight/day. However, the dose is not limited to these.

When the medicinally active substance of the present invention is used as an anticancer agent, examples of cancers to be treated include those having features of malignant tumors such as solid tumors including adenocarcinoma, epithelioma, sarcoma, glioma, melanoma and lymphoma, and a fluid cancer such as leukemia.

EXAMPLES

The present invention will now be described by way of its Examples. However, the present invention is not limited to these Examples.

Synthesis Example

Preparation steps of a sulfopyranosylacylglycerol derivative will be shown in Scheme 2 by way of a sulfoquinovosylacylglycerol α derivative.

Scheme 2

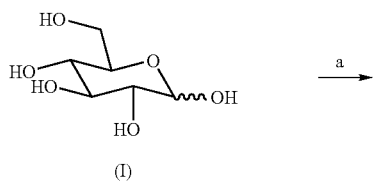

(I)

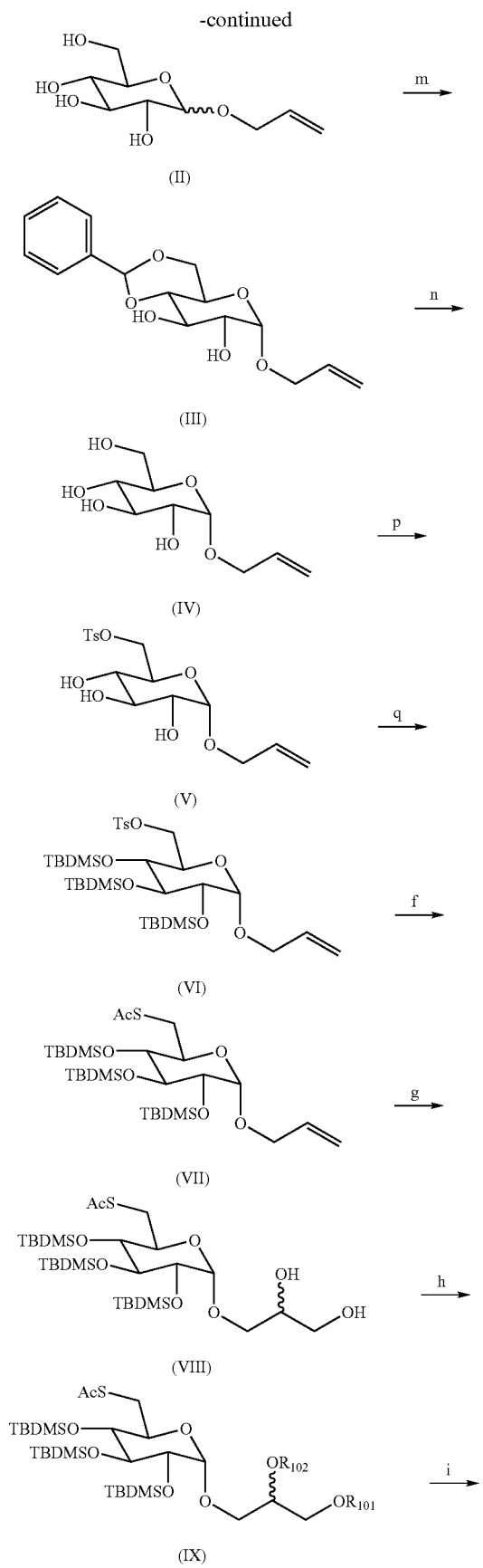
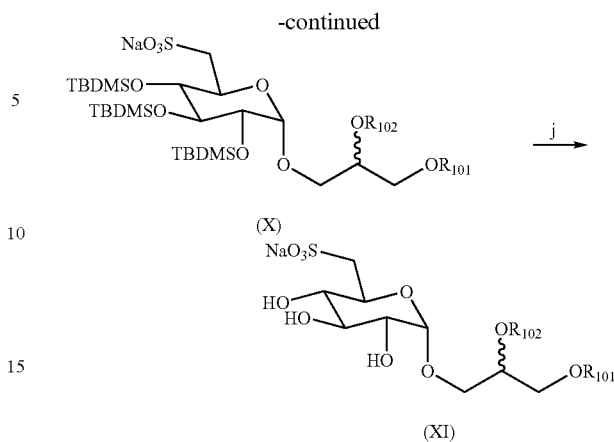

Ts=tosyl, TBDMS=t-butyldimethylsilyl, AcS=acetylthio, $R_{101}$=an acyl residue of an unsaturated higher fatty acid, and $R_{102}$=a hydrogen atom or an acyl residue of an unsaturated higher fatty acid.

Reaction Conditions:
a; allyl alcohol, trifluoromethanesulfonic acid, at 80° C.
m; benzaldehyde, zinc chloride, at room temperature
n; acetic acid, water, at 100° C.
p; toluenesulfonyl chloride, dimethylaminopyridine, pyridine, at room temperature
q; t-butyldimethylsilyl trifluoromethanesulfonate, 2,6-lutidine, dichloromethane, at room temperature
f; potassium thioacetate, ethanol, under reflux
g; osmium tetraoxide, trimethylamine N-oxide dihydrate, t-butanol, water
h; fatty acid, 1-ethyl-3-(3-dimethylaminopropyl)-carbodiimide hydrochloride (EDCI), at room temperature
i; OXONE, glacial acetic acid, potassium acetate, at room temperature
j; acetic acid, tetrahydrofuran, trifluoroacetic acid, water, at room temperature Scheme 2 is the same as those of Scheme 1 except for Steps B to E of Scheme 1. More specifically, in Scheme 2, Step m is employed instead of Step B in Scheme 1. In Step m, compound (II) is reacted with benzaldehyde to prepare a benzylidene derivative. By virtue of this reaction, α-anomer is crystallized and separated.

In the reaction of Scheme 2, p-toluenesulfonyl chloride is reacted with compound (IV) thereby to bond a tosyl group at C6 carbon thereof in Step p, and then, the C2, C3 and C4 carbons are protected with t-butyldimethylsilyl groups (Step q). In this case, Step B of protecting the C6 carbon by an alkyl or substituted silyl group, and Step D of deprotecting the C6 carbon in the process of Scheme 1 may be omitted, because of the stable nature of the tosyl group.

Furthermore, in Step h, a mixture of a monoester and diester is obtained. The monoester and the diester are separated from each other by chromatography and subjected to Step i, respectively.

Example 1

Route a: 1-O-(2-propenyl)-D-glucose (II)
One hundred grams of D-glucose (I) was added into 250 mL of allyl alcohol and sufficiently dissolved therein. To the solution, 0.8 mL of trifluoromethanesulfonic acid was gradually added under an ice-cooled condition. Then, the solution was reacted in an oil bath at 80° C. for 30 hours while stirring. At the stage where the reaction sufficiently proceeded, the reaction mixture was neutralized with 1 mL of trimethylamine and concentrated in vacuo. The thin layer chromatography demonstrated a yield of about 60–70%.

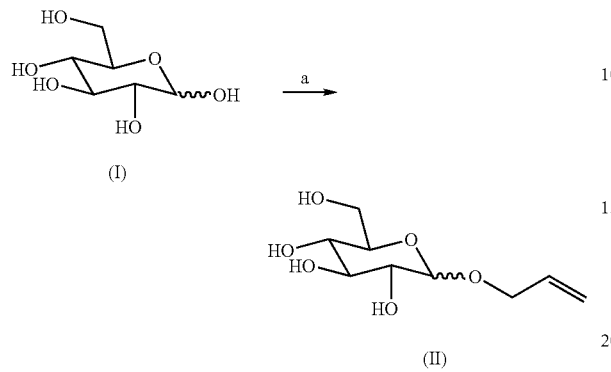

Route m: 1-O-(2-propenyl)-4,6-O-benzylidene-α-D-glucose (III)

37.5 grams of the compound (II) was added to 210 mL of benzaldehyde and dissolved well. To the solution, 98 g of zinc chloride was added. The reaction mixture was reacted at room temperature for 4 hours. Thereafter, the reaction mixture was added to 500 mL of hexane, and then 100 mL of diluted sodium hydrogencarbonate was added. The reaction mixture was allowed to stand at 0° C. for 30 minutes to crystallize. The crystal was filtered with suction, and dissolved in 50 mL of ethanol. The solution was allowed to stand at 0° C. for 30 minutes for recrystallization (yield: 21 g (68.1 mmol), recovery: 40.0%).

$^1$H NMR (300 MHz, CDCl$_3$+TMS); 7.51–7.49(2H, m, Ar), 7.38–7.33(3H, m, Ar), 5.98–5.85(1H, m, —C$\underline{H}$=CH$_2$), 5.51(1H, s, Ar—C$\underline{H}$), 5.31(1H, dd, J=1.5&15.9, —CH=C$\underline{H}_2$), 5.23(1H, dd, J=1.2&10.4, —CH=C$\underline{H}_2$), 4.90(1H, d, J=3.9, H-1), 4.28–4.19(2H, m, —C$\underline{H}_2$—CH=CH$_2$), 4.06–4.00(1H, m, H-5), 3.93(1H, t, J=9.3, H-3), 3.87–3.78 (1H, m, H-6a), 3.70(1H, t, J=10.2, H-2), 3.60(1H, dd, J=3.8&9.2, H-6b), 3.47(1H, t, J=9.3, H-4)

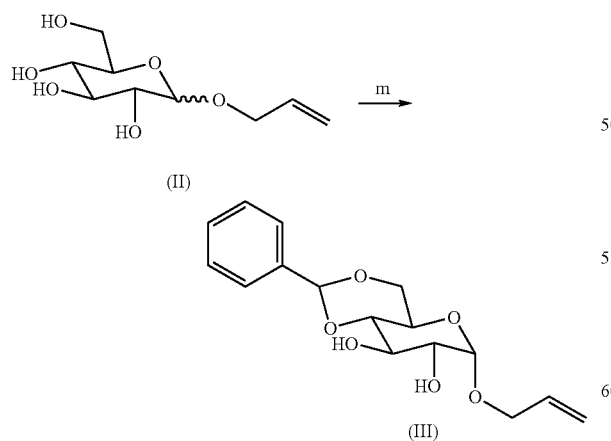

Route n: 1-O-(2-propenyl)-α-D-glucose (IV)

Into 260 mL of a solution of acetic acid and water (8:5), 10.7 g (34.7 mmol) of the compound (III) was dissolved. The solution was reacted at 100° C. for 1 hour, concentrated in vacuo, and purified by silica gel flash chromatography (dichloromethane:methanol=6:1) (yield: 6.3 g (28.6 mmol), recovery: 82.4%).

$^1$H NMR (300 MHz, CD$_3$OD+TMS); 5.92–5.79(1H, m, —C$\underline{H}$=CH$_2$), 5.26–5.18(1H, m, —CH=C$\underline{H}_2$), 5.07–5.03 (1H, m, —CH=C$\underline{H}_2$), 4.23–3.23(7H, m)

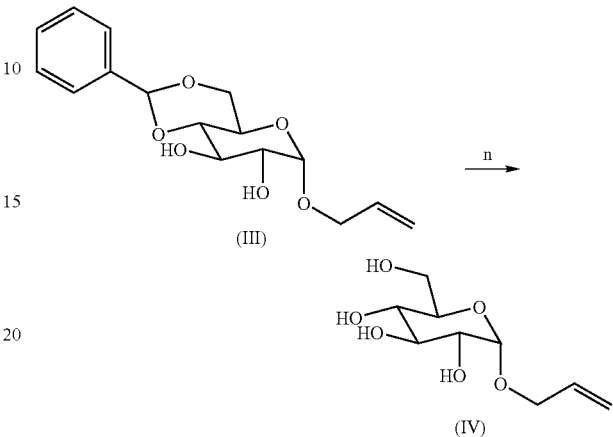

Route p: 1-O-(2-propenyl)-6-O-(4-tolylsulfonyl)-α-D-glucose (V)

Into 200 mL of anhydrous pyridine, 6.3 g (28.6 mmol) of the compound (IV) was dissolved, and 195 mg of p-dimethylaminopyridine (DMAP) and 7.0 g of p-toluenesulfonyl chloride were added. The solution was reacted for 16 hours at room temperature while stirring. Thereafter, the reaction was quenched by adding 20 mL of cold distilled water, and the reaction mixture was extracted with ethyl acetate (3×200 mL). The organic layers were combined, neutralized to pH 4 with 1.0 M and 0.1 M hydrochloric acids, washed with brine (2×200 mL), dried over anhydrous sodium sulfate, filtered, concentrated in vacuo, and purified by silica gel flash chromatography (dichloromethane:methanol=20:1) (yield: 8.6 mg (23.0 mmol), recovery: 83.8%).

$^1$H NMR (300 MHz, CDCl$_3$+TMS); 7.77(2H, d, J=8.3, Ar at TsCH$_3$), 7.30(2H, d, J=8.1 Ar at TsSO$_2$), 5.90–5.77(1H, m, —C$\underline{H}$=CH$_2$), 5.24(1H, dd, J=1.4&17.2, —CH=C$\underline{H}_2$), 5.11(1H, dd, J=1.2&12.4, —CH=C$\underline{H}_2$), 4.79(1H, d, J=3.3, H-1), 4.38–3.38(8H, m), 2.40(3H, s, TSC$\underline{H}_3$)

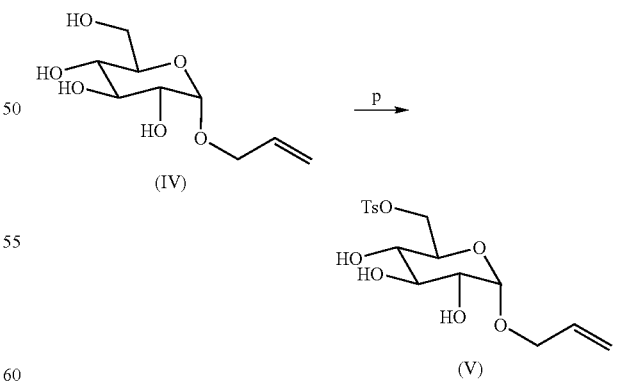

Route q: 2,3,4-tri-O-(t-butyldimethylsilyl)-1-O-(2-propenyl)-6-O-(4-tolylsulfonyl)-α-D-glucose (VI)

Into 25 mL of anhydrous dichloromethane, 11.2 g (29.9 mmol) of the compound (V) was dissolved and 23.8 g of t-butyldimethylsilyl trifluoromethanesulfonate and 14.4 g of 2,6-lutidine were added. The solution was reacted under nitrogen flow for 16 hours while stirring. Thereafter, the reaction was quenched by adding 150 mL of dichloromethane, and the reaction mixture was washed with brine (2×100 mL), dried over anhydrous sodium sulfate, filtered, concentrated in vacuo, purified by silica gel flash chromatography (hexane:ethyl acetate=30:1) (yield: 19.6 g (27.4 mmol), recovery: 91.6%).

¹H NMR (300 MHz, CDCl₃+TMS); 7.83(2H, d, J=8.3, Ar at TsCH₃), 7.29(2H, d, J=8.0, Ar at TsSO₂), 5.92–5.79(1H, m, —C$\underline{H}$=CH₂), 5.21(1H, dd, J=1.5&17.2, —CH=C$\underline{H}_2$), 5.11(1H, d, J=10.4, —CH=C$\underline{H}_2$), 4.67(1H, d, J=2.8, H-1), 4.30–3.44(8H, m), 2.41(3H, s, TSC$\underline{H}_3$), 0.91–0.78(27H, m, C$\underline{H}_3$ at t-Bu), 0.13–-0.02(18H, m, Si—C$\underline{H}_3$)

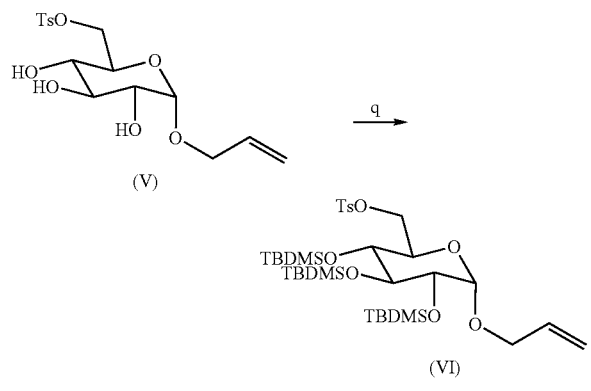

Route f: 2,3,4-tri-O-(t-butyldimethylsilyl)-1-O-(2-propenyl)-6-deoxy-6-acetylthio-α-D-glucose (VII)

Into 20 mL of anhydrous ethanol, 7.9 g (11.0 mmol) of the compound (VI) was dissolved, and then 1.8 g of potassium thioacetate was added. The solution was reacted under reflux for 3 hours while stirring. Thereafter, the reaction was quenched by adding 100 mL of cold distilled water, and the reaction mixture was extracted with ethyl acetate (3×200 ml). The organic layers were combined, washed with brine (2×200 mL), dried over anhydrous sodium sulfate, filtered, concentrated in vacuo, and purified by silica gel flash chromatography (hexane:ethyl acetate=50:1) (yield: 5.6 g (9.02 mmol), recovery: 82.0%).

¹H NMR (300 MHz, CDCl₃+TMS); 5.97–5.81(1H, m, —C$\underline{H}$=CH₂), 5.26(1H, dd, J=1.6&17.2, —CH=C$\underline{H}_2$), 5.13(1H, dd, J=1.6&10.4, —CH=C$\underline{H}_2$), 4.73(1H, d, J=3.2, H-1), 4.32–3.42(7H, m), 2.83(1H, dd, J=9.8&13.3, H-6b), 2.30(3H, s, SCOC$\underline{H}_3$), 0.91–0.82(27H, m, C$\underline{H}_3$ at t-Bu), 0.12–-0.03(18H, m, Si—C$\underline{H}_3$)

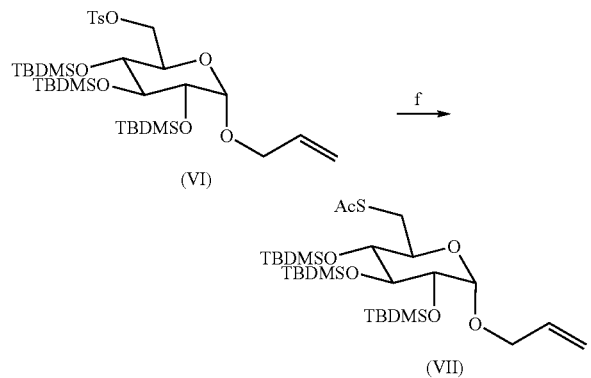

Route g: 3-O-[2,3,4-tri-O-(t-butyldimethylsilyl)-6-deoxy-6-acetylthio-α-D-glucopyranosyl]-glycerol (VIII)

Into a mixture of t-butanol:H₂O (=4:1), 5.6 g (9.02 mmol) of the compound (VII) was dissolved and then 1.5 g of trimethylamine N-oxide dihydrate and 15 mL of 0.04 M solution of osmium tetraoxide in t-butanol were added. The solution was reacted at room temperature for 22 hours while stirring. Thereafter, 15 g of activated charcoal was added, and the reaction mixture was allowed to stand while stirring for 1.5 hours to adsorb the osmium tetraoxide. After filtration with suction, the reaction was quenched by adding 200 mL of cold distilled water, and extracted with ethyl acetate (3×200 mL). The organic layers were combined, washed with brine (2×300 mL), dried over anhydrous sodium sulfate, filtered, concentrated in vacuo, and purified by silica gel flash chromatography (hexane:ethyl acetate=3:1→2:1) (yield: 5.2 g (7.94 mmol), recovery: 88.0%).

¹H NMR (300 MHz, CDCl₃+TMS); 4.73(1H, m, H-1(R and S)), 4.12–3.40(10H, m), 2.86(1H, dd, J=9.2&13.6, H-6b), 2.32(3H, s, SCOC$\underline{H}_3$), 0.88–0.79(27H, m, C$\underline{H}_3$ at t-Bu), 0.08–-0.03(18H, m, Si—C$\underline{H}_3$)

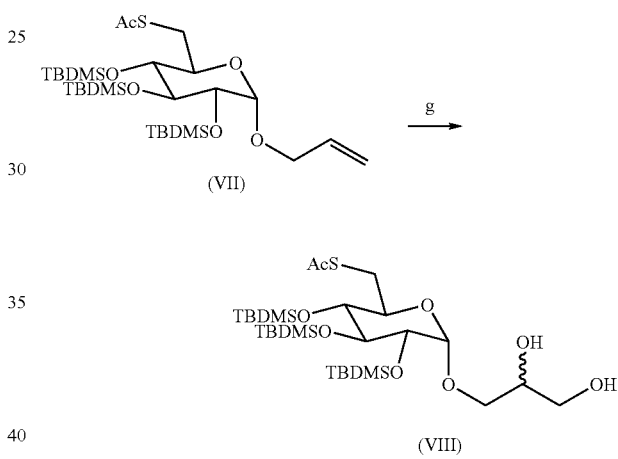

Route h: 3-O-[2,3,4-tri-O-(t-butyldimethylsilyl)-6-deoxy-6-acetylthio-α-D-glucopyranosyl]-1-O-oleoyl-glycerol (IX) and 3-O-[2,3,4-tri-O-(t-butyldimethylsilyl)-6-deoxy-6-acetylthio-α-D-glucopyranosyl]-1,2-di-O-oleoyl-glycerol (IX')

Into 20 mL of anhydrous dichloromethane, 1.37 g (2.09 mmol) of the compound (VIII) was dissolved and then 600 mg of EDCl, 26 mg of DMAP and 660 mg of oleic acid were added. The solution was reacted at room temperature for 16 hours while stirring. Thereafter, the reaction was quenched by adding 200 mL of dichloromethane, and washed with brine (2×100 mL), dried over anhydrous sodium sulfate, filtered, concentrated in vacuo, and purified by silica gel flash chromatography (hexane:ethyl acetate=20:1→10:1→7:1) (yield of the diester: 772 mg (652 μmol) and yield of the monoester: 895 mg (974 μmol); recovery (both esters in total) of 78.0%).

¹H NMR (300 MHz, CDCl₃+TMS); 5.32–5.28(2H, m, —C$\underline{H}$=C$\underline{H}$—), 4.68(1H, m, H-1(R and S)), 3.98–3.36(10H, m), 2.81(1H, dd, J=9.5&13.4, H-6b), 2.32–2.27(5H, m, OCOC$\underline{H}_2$&SCOC$\underline{H}_3$), 1.98–1.93(4H, m, C$\underline{H}_2$—CH=CH—C$\underline{H}_2$), 1.61–1.56(2H, m, OCOCH₂C$\underline{H}_2$), 1.28–1.23(20H, br, —C$\underline{H}_2$—), 0.88–0.79(30H, m, C$\underline{H}_3$ at t-Bu & C$\underline{H}_3$ at Acyl), 0.09–-0.04(18H, m, Si—C$\underline{H}_3$)(NMR of the monoester)

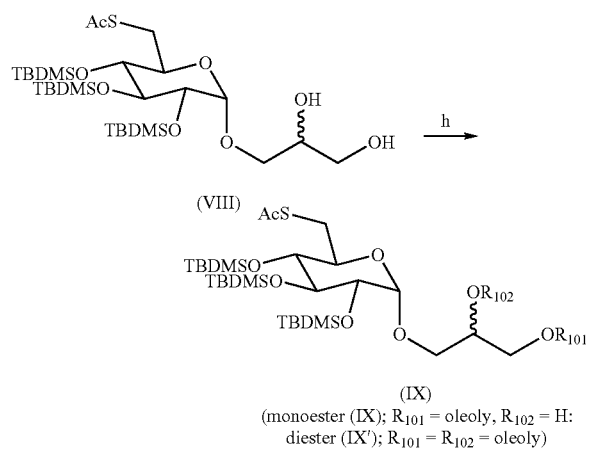

(VIII)

(IX)
(monoester (IX); R_{101} = oleoyl, R_{102} = H:
diester (IX'); R_{101} = R_{102} = oleoyl)

Route i: 3-O-[2,3,4-tri-O-(t-butyldimethylsilyl)-6-deoxy-6-sulfo-α-D-glucopyranosyl]-1-O-oleoyl-glycerol Sodium Salt (X)

Into 3.5 mL of glacial acetic acid, 21.4 mg (23.2 μmol) of the compound (IX: monoester) was dissolved and then 500 mg of potassium acetate and 35.4 mg of OXONE were added. The mixture was reacted at room temperature for 6 hours while stirring. Thereafter, the reaction was quenched by adding 15 mL of cold distilled water, extracted with ethyl acetate (5×20 mL). The organic layers were combined, neutralized with saturated sodium hydrogencarbonate soltuion (5×70 mL), washed with brine (2×60 mL), dried over anhydrous sodium sulfate, filtered, concentrated in vacuo, and purified by silica gel flash chromatography (dichloromethane:methanol=50:1→20:1). Thereafter, the reaction product was further purified by high performance liquid chromatography (ODS column, methanol:water=80:20) (yield: 3.3 mg (3.49 μmol), recovery: 15.0%).

$^1$H NMR (300 MHz, CDCl$_3$+TMS); 5.16–5.14(2H, br, —C$\underline{H}$=C$\underline{H}$—), 4.60(1H, br, H-1(R and S)), 4.31–2.88(11H, m), 2.17–2.13(2H, br, OCOC$\underline{H}_2$), 1.82–1.80(4H, br, C$\underline{H}_2$—CH=CH—C$\underline{H}_2$), 1.42(2H, br, OCOCH$_2$C$\underline{H}_2$), 1.11 (20H, br, —C$\underline{H}_2$—), 0.72(30H, m, C$\underline{H}_3$ at t-Bu & C$\underline{H}_3$ at Acyl), −0.08(18H, br, Si—C$\underline{H}_3$)

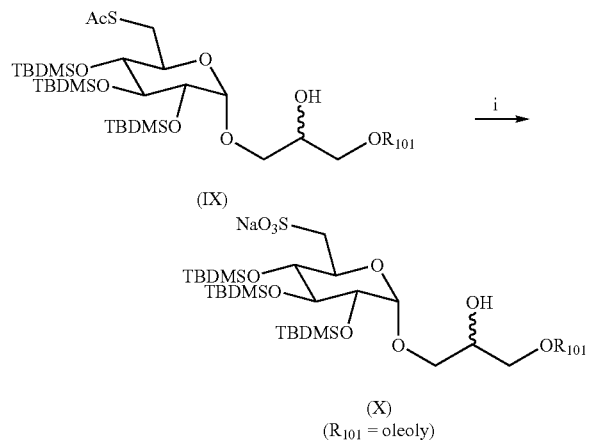

(IX)

(X)
(R_{101} = oleoyl)

Route j: 3-O-(6-deoxy-6-sulfo-α-D-glucopyranosyl)-1-O-oleoyl-glycerol Sodium Salt (XI)

Into 7 mL of a solution of acetic acid, tetrahydrofuran, trifluoroacetic acid and water (3:1:0.4:1), 358.4 mg (378 μmol) of the compound (X) was dissolved. The solution was reacted at room temperature for 16 hours while stirring, and the reaction mixture was extracted with ethyl acetate (3×10 mL). The organic layers were combined, washed with brine (2×20 mL), dried over anhydrous sodium sulfate, filtered, concentrated in vacuo, and purified by silica gel flash chromatography (dichloromethane methanol=10:1→dichloromethane:methanol:water=65:25:4)(yield: 138.1 mg (229 μmol), recovery: 62.7%).

$^1$H NMR (300 MHz, CD$_3$OD+TMS); 5.24–5.17(2H, m, —C$\underline{H}$=C$\underline{H}$—), 4.69(1H, m, H-1(R and S)), 4.18–2.75(11H, m), 2.29–2.21(2H, m, OCOC$\underline{H}_2$), 1.94–1.90(4H, m, C$\underline{H}_2$—CH=CH—C$\underline{H}_2$), 1.49(2H, br, OCOCH$_2$C$\underline{H}_2$), 1.20 (20H, br, —C$\underline{H}_2$—), 0.78(3H, t, J=6.3, C$\underline{H}_3$)

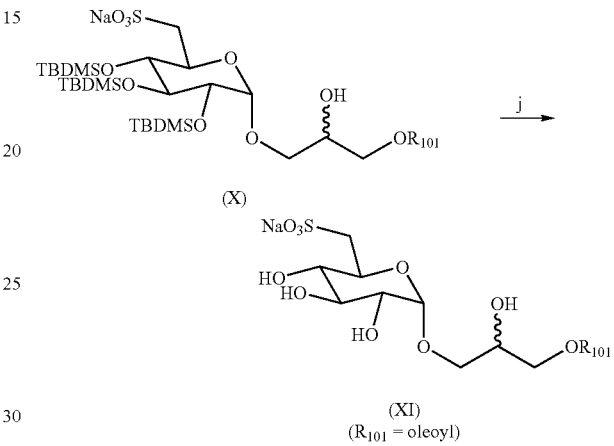

(X)

(XI)
(R_{101} = oleoyl)

Example 2

The Steps h–j were carried out in the same manner as in Example 1 except that myristoleic acid was used in place of oleic acid to synthesize 3-O-(6-deoxy-6-sulfo-α-D-glucopyranosyl)-1-o-myristoleoly-glycerol sodium salt (yield: 118.7 mg (217 μmol), recovery: 59.8%).

Example 3

The same procedure as in Example 2 was repeated except that palmitoleic acid was used in place of oleic acid to synthesize 3-O-(6-deoxy-6-sulfo-α-D-glucopyranosyl)-1-O-palmitoleoyl-glycerol sodium salt (yield: 142 mg (247 μmol), recovery: 67.7%).

Example 4

The same synthesis example as in Example 1, except that the compound (IX': diester) was used in place of the compound (IX: monoester) in the route i of preparing the compound (X) from the compound (IX), and a molybdenum oxidizer was used in place of OXONE, will be described.

13.1 mg (11.0 μmol) of the compound (IX': diester) was dissolved in 0.5 mL of dichloromethane and 0.5 mL of methanol. 50 μL of 0.06M solution of hexaammonium heptamolybdate tetrahydrate ((NH$_4$)$_6$Mo$_7$O$_{24}$·4H$_2$O) in 30% hydrogen peroxide was further added thereto and stirred at room temperature for 50 hours. Thereafter, 10 mL of ethyl acetate was added to the reaction solution, and the resultant solution was washed with saturated sodium hydrogencarbonate solution (2×5 mL) and brine (2×5 mL), dried over anhydrous sodium sulfate, filtered, concentrated in vacuo, and purified by silica gel flash chromatography (dichloromethane:methanol=50:1→10:1). As a result, a colorless oily substance was obtained (yield: 7.8 mg (6.4 μmol), recovery: 58.2%).

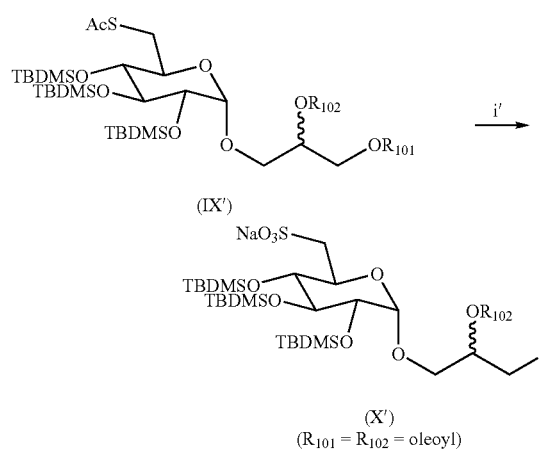

(IX')

(X')
($R_{101} = R_{102}$ = oleoyl)

The compound represented by General Formula (1) of the present invention was subjected to a physiological assay.

<Assay 1>

An assay on inhibitory effect against a DNA polymerase α was carried out in the following manner.

0.05 U of a DNA polymerase α purified and isolated from a bovine thymus by an immunoaffinity column was mixed with each of test compounds, sulfopyranosylacylglycerol (hereinafter, simply referred to as "SQAG") derivatives, namely, SQAG 1, SQAG 2 and SQAG 3 (listed in table 1) dissolved in DMSO. Each mixture was added with a buffer containing inorganic salts for the enzymatic reaction, [$^3$H]-labeled dTTP and compounds for reaction containing a template DNA strand, and incubated at 37° C. for 60 minutes.

After the enzymatic reaction was quenched, the resultant reaction product was fixed on a dedicated filter and subjected to measurement by a liquid scintillation counter. The amount of enzymatically incorporated dTTP was calculated as a radiation dose (cpm) of [$^3$H]. Note that, each of the sulfopyranosylacylglycerol derivatives is a mixture of the S- and R-configurations with respect to an absolute configuration of the carbon of the 2-position of the glycerol moiety.

The results are shown as $IC_{50}$ in Table 1 below.

As is clear from Table 1, the compounds subjected to the assay exhibit significant inhibitory activity against the DNA polymerase α.

Colon cancer cells and gastric cancer cells used in the following two assays are only for the purpose of illustration of cancer cells for which the medicinally active agent of the present invention effectively works. Thus, cancer cells for which the medicament of the invention is effective are not limited to these. Examples of other cancer cells include those of esophageal cancer, gastric cancer, colon cancer, including those at colon and recta, thyroid cancer, bladder cancer, kidney cancer, prostatic cancer, malignant lymphoma, brain tumor, lung cancer, laryngeal cancer, pharyngeal cancer, hepatic cancer, gallbladder cancer, bile duct cancer, pancreas cancer, breast cancer, uterine cancer, ovarian cancer, vaginal cancer, leukemia, childhood cancer, skin cancer, osteosarcoma, tongue cancer, cancer of small intestine, penile cancer, urethral cancer, ureteral cancer, testicular cancer, thymoma and myeroma.

<Assay 2>

An assay on anticancer activity against cultured colon cancer cells was carried out in the following manner.

Colon cancer cells DLD-1 were maintained and subcultured in RPMI 1640 medium (containing 10% calf serum). Each of the test compounds (SQAG 2, SQAG 3 shown in Table 1) was suspended and diluted in the medium, and then the cancer cells were cultivated together with the medium in a 96-well plate at $3\times10^3$ cells/well. After 48 hour cultivation, the MTT assay (Mosmann, T: Journal of Immunological Method, 65, 55–63 (1983)) was carried out to compare survival rates.

The results are shown in FIG. 1.

In FIG. 1, open squares connected by a solid line indicate SQAG2 and open circles connected by a solid line indicate SQAG3.

As is clear from FIG. 1, all of the sulfopyranosylacylglycerol derivatives have significant anticancer activities against the colon cancer cells used.

<Assay 3>

An assay on anticancer activity against cultured gastric cancer cells was carried out in the same manner as in the

TABLE 1

Inhibitory activity on DNA polymerase α

| Compound | $R_{101}$ | DNA polymerase inhibitory activity $IC_{50}$ (μg/mL) |
|---|---|---|
| SQAG1 (14:1) | $CH_3$—$(CH_2)_3$—$(CH=CH—CH_2)_1$—$(CH_2)_6$—CO— | 9.0 |
| SQAG2 (16:1) | $CH_3$—$(CH_2)_5$—$(CH=CH—CH_2)_1$—$(CH_2)_6$—CO— | 5.5 |
| SQAG3 (18:1) | $CH_3$—$(CH_2)_7$—$(CH=CH—CH_2)_1$—$(CH_2)_6$—CO— | 2.0 | assay 2 except that gastric cancer cells NUGC-3 were used instead of the colon cancer cells DLD-1.

The results are shown also in FIG. 1.

In FIG. 1, solid squares connected by a solid line indicate SQAG2 and solid circles connected by a solid line indicate SQAG3.

As is clear from FIG. 1, the sulfopyranosylacylglycerol derivatives have anticancer activities against the gastric cancer cells used.

<Assay 4>

Tests for human cancer-cell implanted mice were conducted in the following manner.

$5 \times 10^5$ of human lung cancer cells A-549 cultured in an MEM medium containing 5% calf serum were implanted in nude mice BALB/cAcl-nu. The size of the tumor formation site was periodically measured. When the size of the tumor reached 30–50 mm$^3$ (42 days after the implantation), the mice were subjected to an administration test.

Five mice were assigned at random to test groups and a control group. A test compound (SQAG1, SQAG2 and SQAG3 listed in Table 1) suspended in PBS in a concentration of 100 µg/100 µL was administered to the test groups, and PBS was administered to the control group at a dose of 100 µL, every 3 days. This administration operation was repeated 8 times. The size of the tumor formation site was measured at all the administration times. The volume of the tumor was calculated in accordance with the following formula.

Volume of tumor=tumor-site length×(tumor site width)$^2$×0.5

Figure 2:
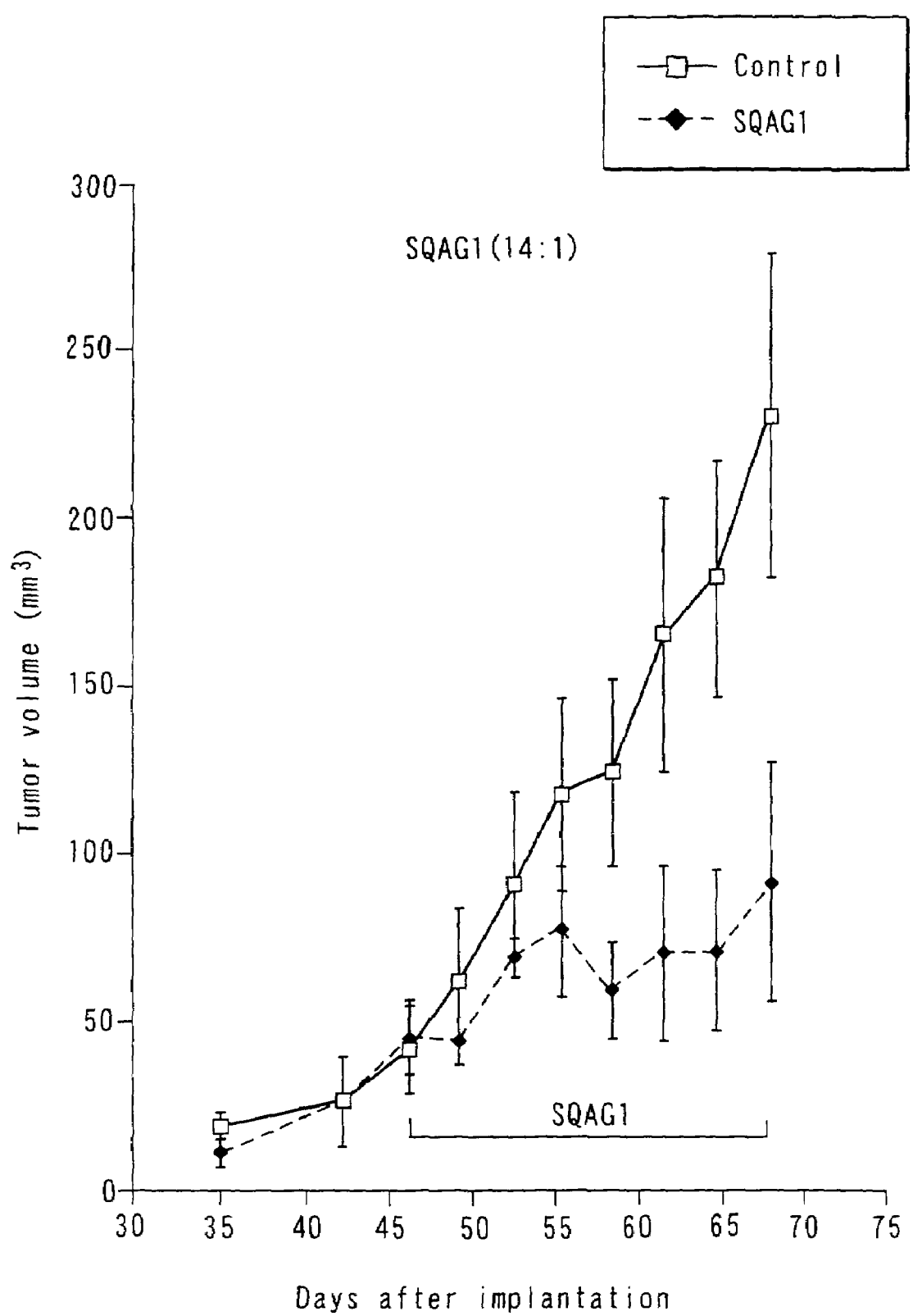
FIG. 2 shows an anticancer activity of a medicament of the present invention obtained by an animal test.
Figure 3:
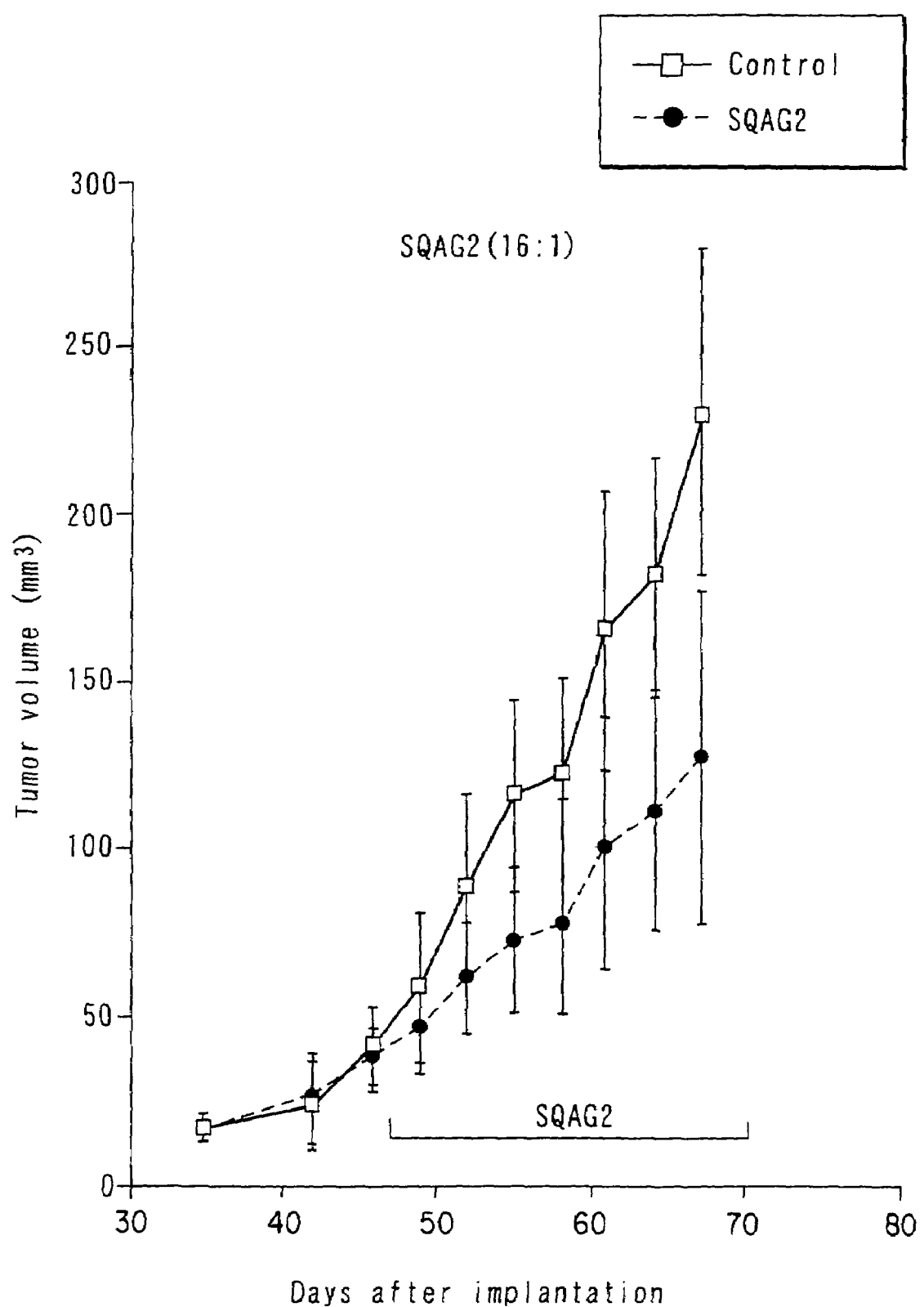
FIG. 3 shows an anticancer activity of a medicament of the present invention obtained by an animal test.
Figure 4:
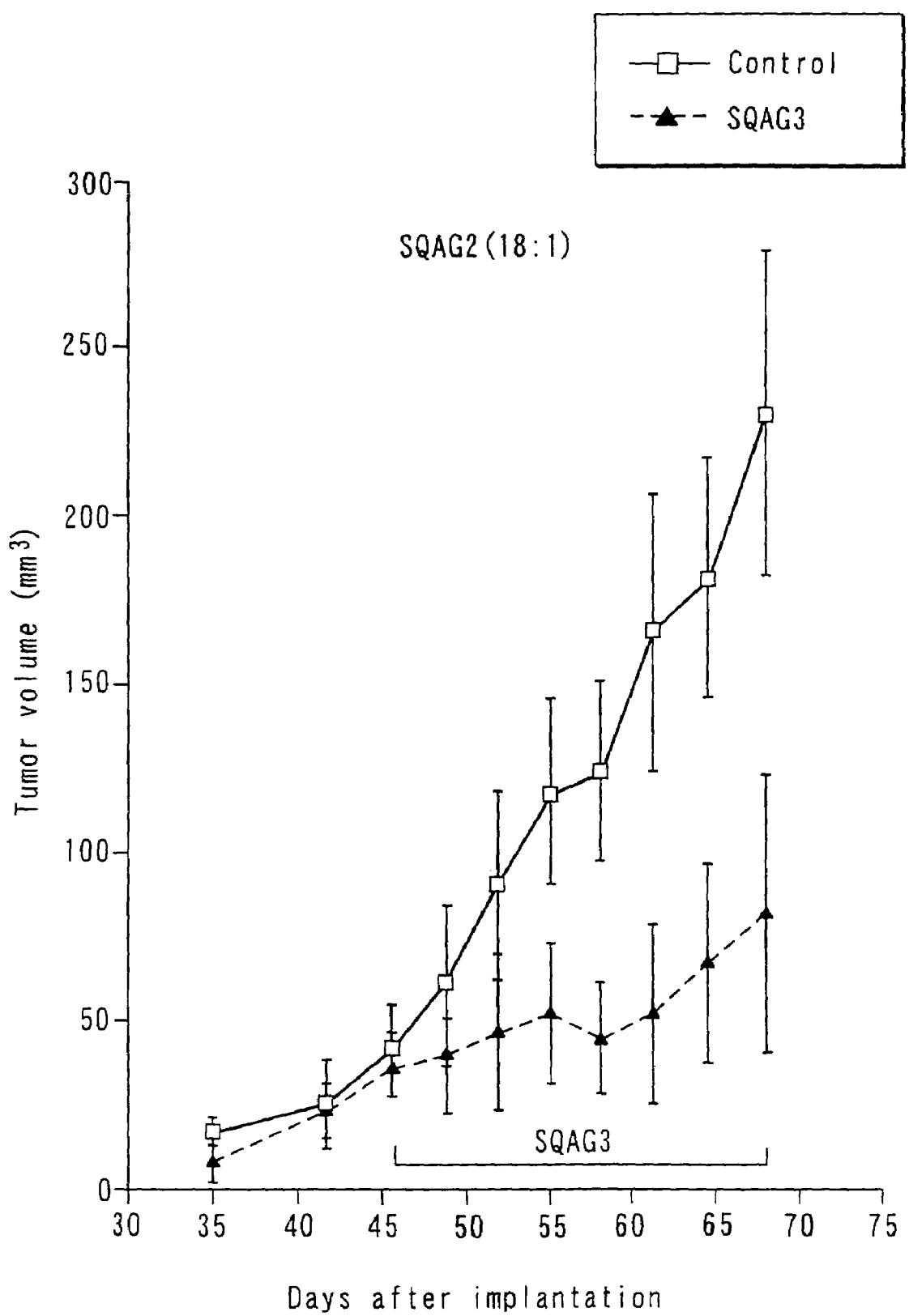
FIG. 4 shows an anticancer activity of a medicament of the present invention obtained by an animal test.

The results obtained for the test compounds are respectively shown in FIG. 2 (SQAG1), FIG. 3 (SQAG2) and FIG. 4 (SQAG3).

In each Figure, the horizontal axis represents days after implantation of the cancer-cell and the vertical axis represents the volume of a tumor.

It was demonstrated that each of the test compounds significantly suppresses the formation of the tumor, compared to the control group.

No particular change was observed in the state of mice in the test groups at the aforementioned dose. The mice were alive in the same state as in the control group.

<Assay 5>

$5 \times 10^5$ of cultured lung cancer cells A-549 were subcutaneously injected into each of 7 week-old female nude mice BALB/cAcl-nu having 20–22 g weight, and the size of tumor was measured every 3 days from 37 days after the implantation. At 43 days after the implantation when the sizes of the tumor in all of the tumor-bearing mice reach 25–35 mm$^3$, the mice were randomly divided into 7 groups of 4 mice for each. Of the 7 groups, one is used as a control group. 100 µL of PBS was subcutaneously injected into the mice of the control group. To the remaining 6 groups, SQAG1(14:1), SQAG2(16:1) and SQAG3(18:1) were subcutaneously injected by dissolving each of the test compounds in 100 µL of PBS so as to give doses of 4 mg and 20 mg per 1 kg weight. The injection was performed every 3 days. This administration operation was repeated from 43 days to 64 days after the cancer-cell implantation. The size of the tumor was measured every 3 days until 70 days after the implantation. The volume of the tumor was calculated in the same manner as in Assay 4.

Figure 5:
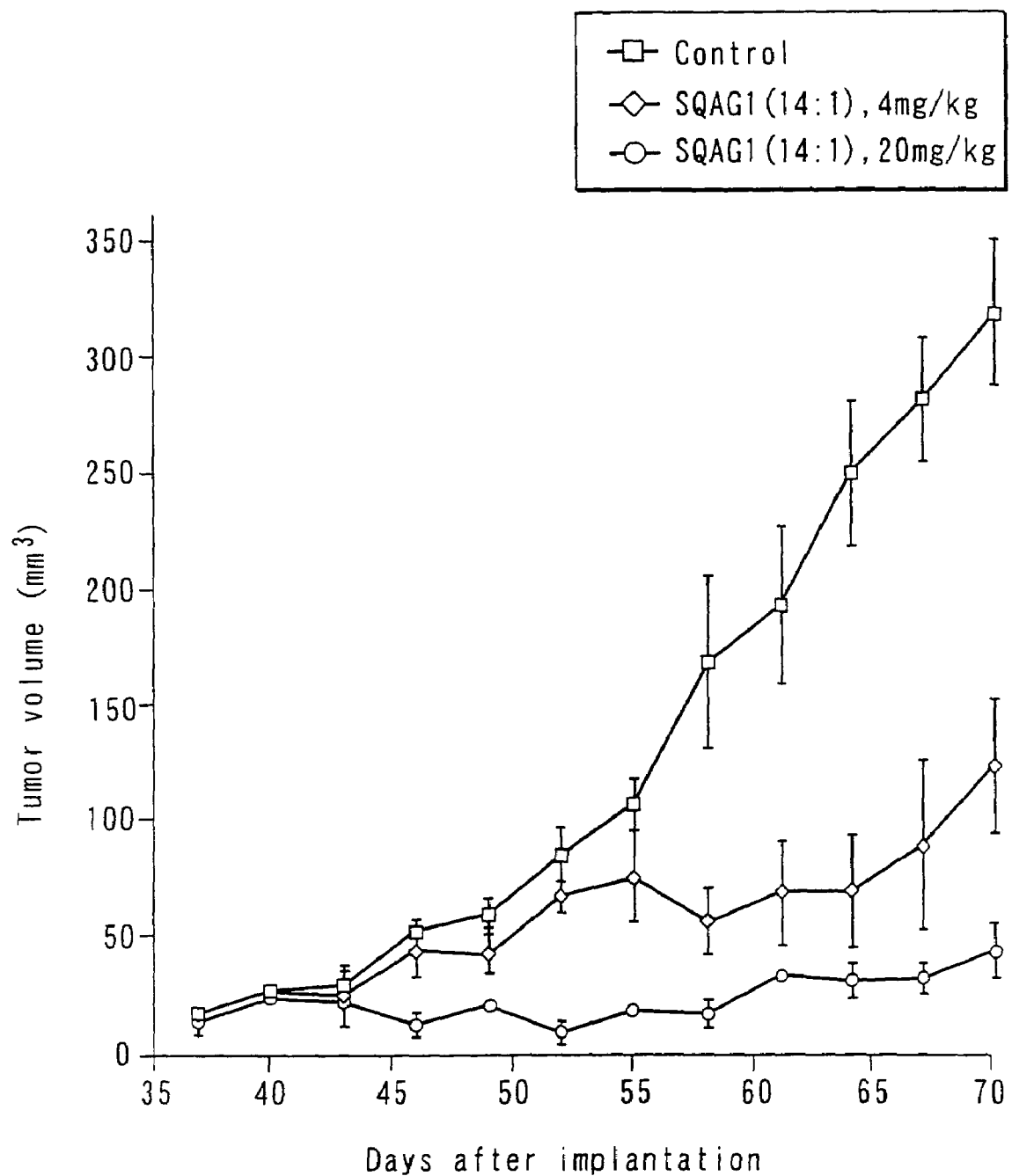
FIG. 5 shows an anticancer activity of a medicament of the present invention obtained by an animal test.
Figure 6:
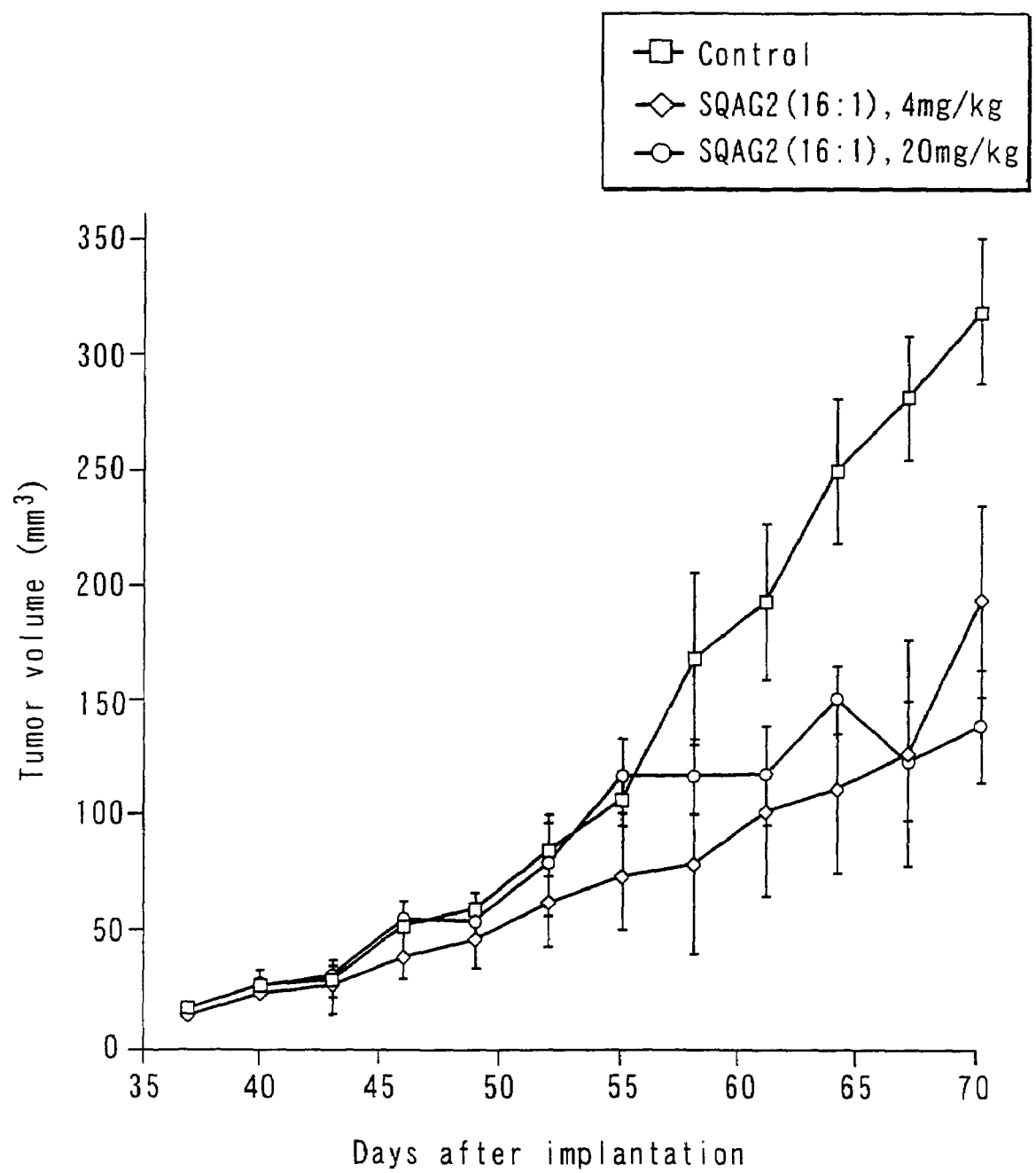
FIG. 6 shows an anticancer activity of a medicament of the present invention obtained by an animal test.
Figure 7:
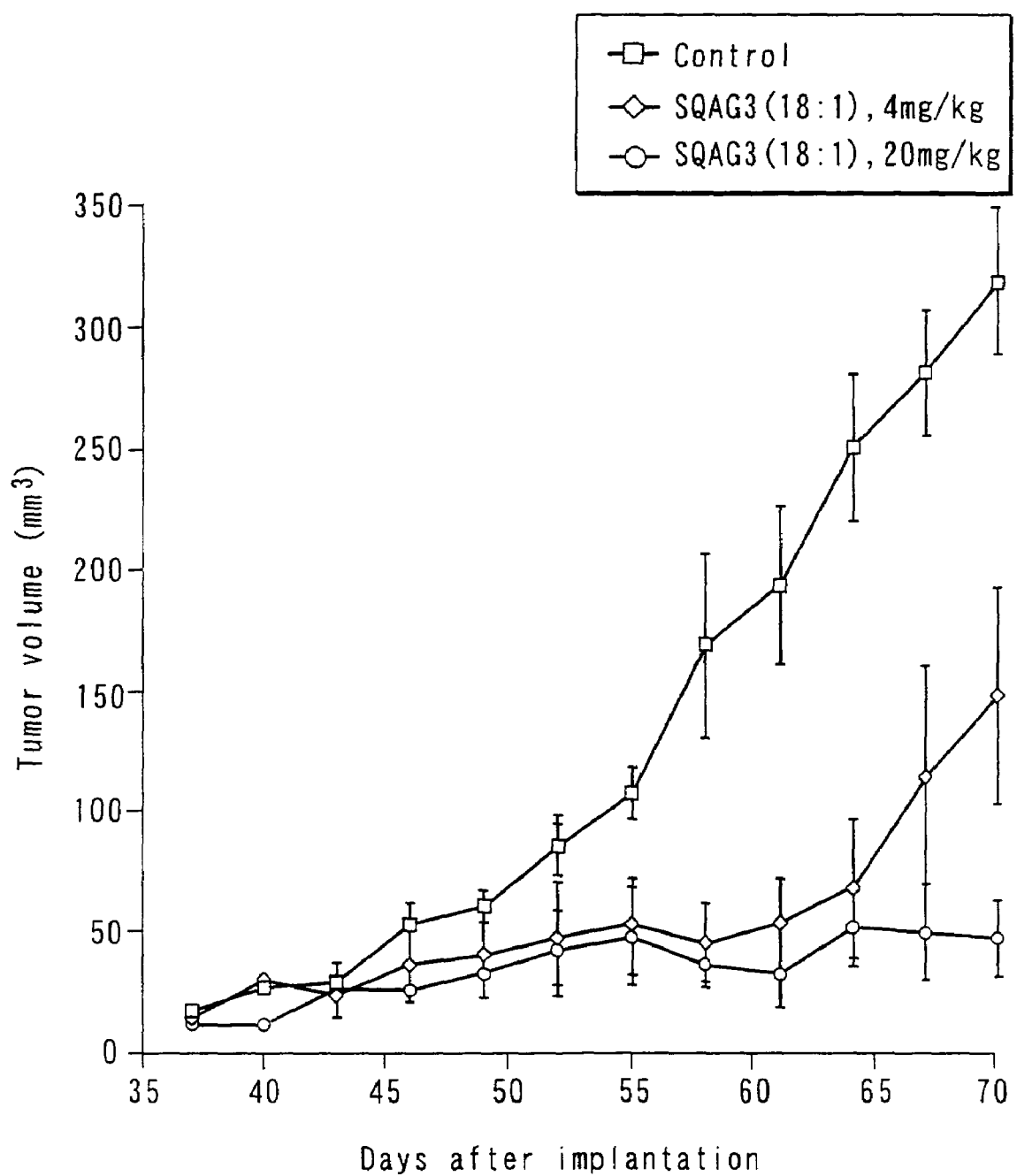
FIG. 7 shows an anticancer activity of a medicament of the present invention obtained by an animal test.

The results obtained for the test compounds are respectively shown in FIG. 5 (SQAG1), FIG. 6 (SQAG2) and FIG. 7 (SQAG3).

In each of the test groups, it was demonstrated that the formation of the tumors is significantly suppressed compared to the control group.

After completion of the test, major organs, such as lung, heart, stomach, liver, pancreas, kidney, intestine and brain, of all the mice of each administration group were subjected to pathological evaluation, and no pathologically abnormality was observed in any organ.

As explained in the foregoing, according to the present invention, there is provided a medicament containing at least one compound selected from the group consisting of sulfopyranosylacylglycerol derivatives represented by General Formula (1) and pharmaceutically acceptable salts thereof, as an active ingredient.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for treating a cancer excluding adenocarcinoma, the cancer being selected from the group consisting of epithelioma, glioma, sarcoma, melanoma, lymphoma and leukemia, comprising administering to a subject in need thereof and suffering from said cancer, a pharmaceutically effective amount of a sulfoquinovosylacylglycerol compound represented by formula (1):

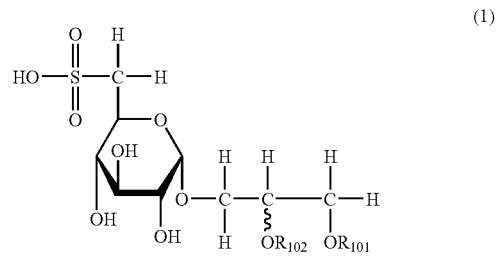

wherein $R_{101}$ represents an acyl residue of an unsaturated higher fatty acid, and $R_{102}$ represents a hydrogen atom, and/or a pharmaceutically acceptable salt thereof.

2. The method according to claim 1, wherein said $R_{101}$ of formula (1) is represented by formula:

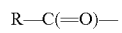

wherein R is a straight-chain aliphatic unsaturated hydrocarbon group having 13–25 carbon atoms and including 1–6 unsaturated bonds.

3. The method according to claim 2, wherein for R, the number of carbon atoms is selected from odd numbers from the group consisting of 13, 15, 17, 19, 21, 23 and 25.

4. The method according to claim 3, wherein $R_{101}$ of formula (1) is

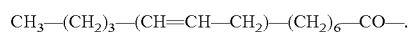

5. The method according to claim 3, wherein $R_{101}$ of formula (1) is

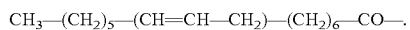
$CH_3—(CH_2)_5—(CH{=}CH—CH_2)—(CH_2)_6—CO—$.

6. The method according to claim 3, wherein $R_{101}$ of formula (1) is

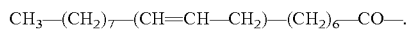
$CH_3—(CH_2)_7—(CH{=}CH—CH_2)—(CH_2)_6—CO—$.

7. The method according to claim 1, wherein the cancer is epithelioma.

8. The method according to claim 1, wherein the cancer is glioma.

9. The method according to claim 1, wherein the cancer is sarcoma.

10. The method according to claim 1, wherein the cancer is melanoma.

11. The method according to claim 1, wherein the cancer is lymphoma.

12. The method according to claim 1, wherein the cancer is leukemia.

* * * * *